(12) United States Patent
Yu

(10) Patent No.: US 12,150,997 B1
(45) Date of Patent: *Nov. 26, 2024

(54) COMPOUND, A CONJUGATE AND USES THEREOF

(71) Applicant: SynerK Biotech Limited, Hong Kong (HK)

(72) Inventor: Dong Yu, Westboro, MA (US)

(73) Assignee: Synerk Biotech Limited (HK)

( * ) Notice: Subject to any disclaimer, the term of this patent is extended or adjusted under 35 U.S.C. 154(b) by 0 days.

This patent is subject to a terminal disclaimer.

(21) Appl. No.: 18/381,402

(22) Filed: Oct. 18, 2023

Related U.S. Application Data

(63) Continuation of application No. 18/196,092, filed on May 11, 2023.

(51) Int. Cl.
*A61K 47/61* (2017.01)
*A61K 47/54* (2017.01)
*C12N 15/113* (2010.01)

(52) U.S. Cl.
CPC ............ *A61K 47/61* (2017.08); *A61K 47/549* (2017.08); *C12N 15/113* (2013.01)

(58) Field of Classification Search
CPC ..... A61K 47/61; A61K 47/549; C12N 15/113
See application file for complete search history.

(56) References Cited

FOREIGN PATENT DOCUMENTS

| CN | 114763367 | * | 7/2022 | |
|---|---|---|---|---|
| WO | WO-2014179620 A1 | * | 11/2014 | ......... A61K 31/7088 |
| WO | WO-2014179627 A2 | * | 11/2014 | ......... A61K 31/7088 |
| WO | WO-2015042447 A1 | * | 3/2015 | ......... A61K 31/7072 |

OTHER PUBLICATIONS

Nair et al. (J. Am. Chem. Soc. 2014, 136, 16958-16961, Dec. 1, 2014). (Year: 2014).*

* cited by examiner

*Primary Examiner* — Anna R Falkowitz
(74) *Attorney, Agent, or Firm* — Elmore Patent Law Group, P.C.; Joseph C. Zucchero; Carolyn S. Elmore

(57) ABSTRACT

The present disclosure relates to the technical field of small nucleic acid drug delivery, and particularly discloses a compound, a conjugate and uses thereof. The present disclosure provides a nucleic acid drug targeted delivery monomer and conjugate and a preparation method thereof, the monomer and the conjugate which is formed by the monomer and has a specific design structure can specifically deliver an active drug (or small nucleic acid) to a cell receptor (or surface) in a targeted manner and can be combined with the receptor. The conjugate connected with the active drug (or small nucleic acid) can improve the cell penetration capability of the nucleic acid drug and enhance the stability of the nucleic acid drug in cells owing to the structural characteristics of the conjugate, and can effectively solve the problem of directional delivery of the drug. The delivery monomer and the conjugate have the advantages of being simple in preparation process, suitable for delivery of various targeted drugs, very wide in application and the like.

6 Claims, 5 Drawing Sheets

Specification includes a Sequence Listing.

formula (V)

formula (V')

Formula (VIII)

formula (IX)

formula (X)

SEQUENCE LISTING

```
Sequence total quantity: 6
SEQ ID NO: 1            moltype = DNA  length = 21
FEATURE                 Location/Qualifiers
source                  1..21
                        mol_type = other DNA
                        organism = synthetic construct
modified_base           6
                        mod_base = OTHER
                        note = uracil
modified_base           8..9
                        mod_base = OTHER
                        note = uracil
modified_base           11..12
                        mod_base = OTHER
                        note = uracil
modified_base           15
                        mod_base = OTHER
                        note = uracil
modified_base           17
                        mod_base = OTHER
                        note = uracil
modified_base           19
                        mod_base = OTHER
                        note = uracil
modified_base           1
                        mod_base = OTHER
                        note = 2'-fluoro modified
modified_base           3
                        mod_base = OTHER
                        note = 2'-fluoro modified
modified_base           5
                        mod_base = OTHER
                        note = 2'-fluoro modified
modified_base           7
                        mod_base = OTHER
                        note = 2'-fluoro modified
modified_base           9..11
                        mod_base = OTHER
                        note = 2'-fluoro modified
modified_base           13
                        mod_base = OTHER
                        note = 2'-fluoro modified
modified_base           15
                        mod_base = OTHER
                        note = 2'-fluoro modified
modified_base           17
                        mod_base = OTHER
                        note = 2'-fluoro modified
modified_base           19
                        mod_base = OTHER
                        note = 2'-fluoro modified
modified_base           21
                        mod_base = OTHER
                        note = 2'-fluoro modified
modified_base           2
                        mod_base = OTHER
                        note = 2'-methoxy modified
modified_base           4
                        mod_base = OTHER
                        note = 2'-methoxy modified
modified_base           6
                        mod_base = OTHER
                        note = 2'-methoxy modified
modified_base           8
                        mod_base = OTHER
                        note = 2'-methoxy modified
```

```
modified_base          12
                       mod_base = OTHER
                       note = 2'-methoxy modified
modified_base          14
                       mod_base = OTHER
                       note = 2'-methoxy modified
modified_base          16
                       mod_base = OTHER
                       note = 2'-methoxy modified
modified_base          18
                       mod_base = OTHER
                       note = 2'-methoxy modified
modified_base          20
                       mod_base = OTHER
                       note = 2'-methoxy modified
SEQUENCE: 1
aacagtgttc ttgctctata a                                              21

SEQ ID NO: 2           moltype = DNA  length = 23
FEATURE                Location/Qualifiers
source                 1..23
                       mol_type = other DNA
                       organism = synthetic construct
modified_base          1..2
                       mod_base = OTHER
                       note = uracil
modified_base          4
                       mod_base = OTHER
                       note = uracil
modified_base          18
                       mod_base = OTHER
                       note = uracil
modified_base          20..23
                       mod_base = OTHER
                       note = uracil
modified_base          2
                       mod_base = OTHER
                       note = 2'-fluoro modified
modified_base          4
                       mod_base = OTHER
                       note = 2'-fluoro modified
modified_base          6
                       mod_base = OTHER
                       note = 2'-fluoro modified
modified_base          8
                       mod_base = OTHER
                       note = 2'-fluoro modified
modified_base          10
                       mod_base = OTHER
                       note = 2'-fluoro modified
modified_base          14
                       mod_base = OTHER
                       note = 2'-fluoro modified
modified_base          16
                       mod_base = OTHER
                       note = 2'-fluoro modified
modified_base          18
                       mod_base = OTHER
                       note = 2'-fluoro modified
modified_base          20
                       mod_base = OTHER
                       note = 2'-fluoro modified
modified_base          1
                       mod_base = OTHER
                       note = 2'-methoxy modified
modified_base          3
                       mod_base = OTHER
                       note = 2'-methoxy modified
modified_base          5
                       mod_base = OTHER
                       note = 2'-methoxy modified
modified_base          7
                       mod_base = OTHER
                       note = 2'-methoxy modified
modified_base          9
                       mod_base = OTHER
                       note = 2'-methoxy modified
modified_base          11..13
                       mod_base = OTHER
```

```
                    note = 2'-methoxy modified
modified_base       15
                    mod_base = OTHER
                    note = 2'-methoxy modified
modified_base       17
                    mod_base = OTHER
                    note = 2'-methoxy modified
modified_base       19
                    mod_base = OTHER
                    note = 2'-methoxy modified
modified_base       21..23
                    mod_base = OTHER
                    note = 2'-methoxy modified
SEQUENCE: 2
ttatagagca agaacactgt ttt                                              23

SEQ ID NO: 3        moltype = DNA  length = 21
FEATURE             Location/Qualifiers
source              1..21
                    mol_type = other DNA
                    organism = synthetic construct
modified_base       2
                    mod_base = OTHER
                    note = uracil
modified_base       10
                    mod_base = OTHER
                    note = uracil
modified_base       12
                    mod_base = OTHER
                    note = uracil
modified_base       18
                    mod_base = OTHER
                    note = uracil
SEQUENCE: 3
ctaggaggct gtaggcataa a                                                21

SEQ ID NO: 4        moltype = DNA  length = 21
FEATURE             Location/Qualifiers
source              1..21
                    mol_type = other DNA
                    organism = synthetic construct
modified_base       1..3
                    mod_base = OTHER
                    note = uracil
modified_base       5
                    mod_base = OTHER
                    note = uracil
modified_base       9
                    mod_base = OTHER
                    note = uracil
modified_base       16
                    mod_base = OTHER
                    note = uracil
modified_base       19
                    mod_base = OTHER
                    note = uracil
SEQUENCE: 4
tttatgccta cagcctccta g                                                21

SEQ ID NO: 5        moltype = DNA  length = 21
FEATURE             Location/Qualifiers
source              1..21
                    mol_type = other DNA
                    organism = synthetic construct
modified_base       2
                    mod_base = OTHER
                    note = uracil
modified_base       10
                    mod_base = OTHER
                    note = uracil
modified_base       12
                    mod_base = OTHER
                    note = uracil
modified_base       18
                    mod_base = OTHER
                    note = uracil
modified_base       7
                    mod_base = OTHER
                    note = 2'-fluoro modified
```

```
modified_base         9
                      mod_base = OTHER
                      note = 2'-fluoro modified
modified_base         11
                      mod_base = OTHER
                      note = 2'-fluoro modified
SEQUENCE: 5
ctaggaggct gtaggcataa a                                              21

SEQ ID NO: 6          moltype = DNA  length = 23
FEATURE               Location/Qualifiers
source                1..23
                      mol_type = other DNA
                      organism = synthetic construct
modified_base         1..3
                      mod_base = OTHER
                      note = uracil
modified_base         5
                      mod_base = OTHER
                      note = uracil
modified_base         9
                      mod_base = OTHER
                      note = uracil
modified_base         16
                      mod_base = OTHER
                      note = uracil
modified_base         19
                      mod_base = OTHER
                      note = uracil
modified_base         22..23
                      mod_base = OTHER
                      note = uracil
modified_base         2
                      mod_base = OTHER
                      note = 2'-fluoro modified
modified_base         4
                      mod_base = OTHER
                      note = 2'-fluoro modified
modified_base         6
                      mod_base = OTHER
                      note = 2'-fluoro modified
modified_base         14
                      mod_base = OTHER
                      note = 2'-fluoro modified
modified_base         16
                      mod_base = OTHER
                      note = 2'-fluoro modified
SEQUENCE: 6
tttatgccta cagcctccta gtt                                            23
```

COMPOUND, A CONJUGATE AND USES THEREOF

RELATED APPLICATION

This application is a continuation of U.S. application Ser. No. 18/196,092, filed May 11, 2023. The entire teachings of the above application are incorporated herein by reference.

SEQUENCE LISTING

The sequence listing submitted via EFS, in compliance with 37 CFR § 1.52 (e) (5), is incorporated herein by reference. The sequence listing XML file submitted via EFS contains the file "42693004 US1 Seq List.xml", created on Dec. 13, 2023, which is 47,030 bytes in size.

FIELD

The present disclosure relates to the technical field of small nucleic acid drug delivery, in particular to a compound, a conjugate and uses thereof.

BACKGROUND

The delivery system is one of the core key technologies in the development of small nucleic acid drugs, and the kind of delivery system which has been most extensively studied worldwide at present may be the targeted conjugation delivery technology. Although the use of the tissue-specific active agents, represented by specific oligonucleotides and oligonucleotide analogs, as therapeutic agents have made some progress, there remains the requirements for further improvements in their pharmacological properties, such as the targeted delivery of the therapeutic agents to lesions to improve the selectivity, biological activity and efficacies of the therapeutic agents. Targeted conjugation delivery technology has recently emerged as one kind of the most widely researched delivery systems, with particular focus on the targeted delivery to liver.

SUMMARY

The present disclosure aims to solve the existing problems of the prior art and provide a compound, a conjugate and uses thereof.

In order to fulfill the purpose, a first aspect of the present disclosure provides a compound M with a structure represented by formula (V) or (V') as shown in FIG. 4A and FIG. 4B.

In formula (V) or (V'):
A denotes an aptamer with a structure derived from saccharide or polypeptide;
L1 is a straight chain group containing an ether linkage and/or an amide linkage having a length of C1-50;
Z has a structure derived from a first phosphorus-containing compound selected from phosphoramidite, H-phosphate and phosphotriester, and is capable of covalently linking to adjacent groups via a phosphate ester bond or a phosphamide diester bond.

A second aspect the present disclosure provides a conjugate N with a structure shown in formula (VI):

(M)m-R"  (VI)

m on formula (VI) is an integer of 1-4, M has a structure provided by the compound represented by formula (V) or (V') as defined above, and when m is greater than 1, each M are the same or different;
R" has an active site capable of linking with Nu.

A third aspect the present disclosure also provides a conjugate T with a structure of formula (VIII) as shown in FIG. 5.

At least one of M1, M2, and M3 on formula (VIII) has a structure derived from compound M which is same as that defined in the first aspect previously mentioned; M1, M2 and M3 are the same or different.

A fourth aspect of the present disclosure provides an use of the compound M and the conjugates N and T in preparation of a small nucleic acid drug.

The present disclosure provides a nucleic acid drug targeted delivery monomer and conjugate and a preparation method thereof, and the monomer and the conjugate which is formed by the monomer and has a specific design structure can specifically deliver an active drug (or small nucleic acid) to a cell receptor (or surface) in a targeted manner and can be combined with the receptor. The conjugate connected with the active drug (or small nucleic acid) can improve the cell penetration capability of the nucleic acid drug and enhance the stability of the nucleic acid drug in cells owing to the structural characteristics of the conjugate, and can effectively solve the problem of directional delivery of the drug. The delivery monomer and the conjugate have the advantages of being simple in preparation process, suitable for delivery of various targeted drugs, very wide in application and the like.

DETAILED DESCRIPTION

Figure 1:
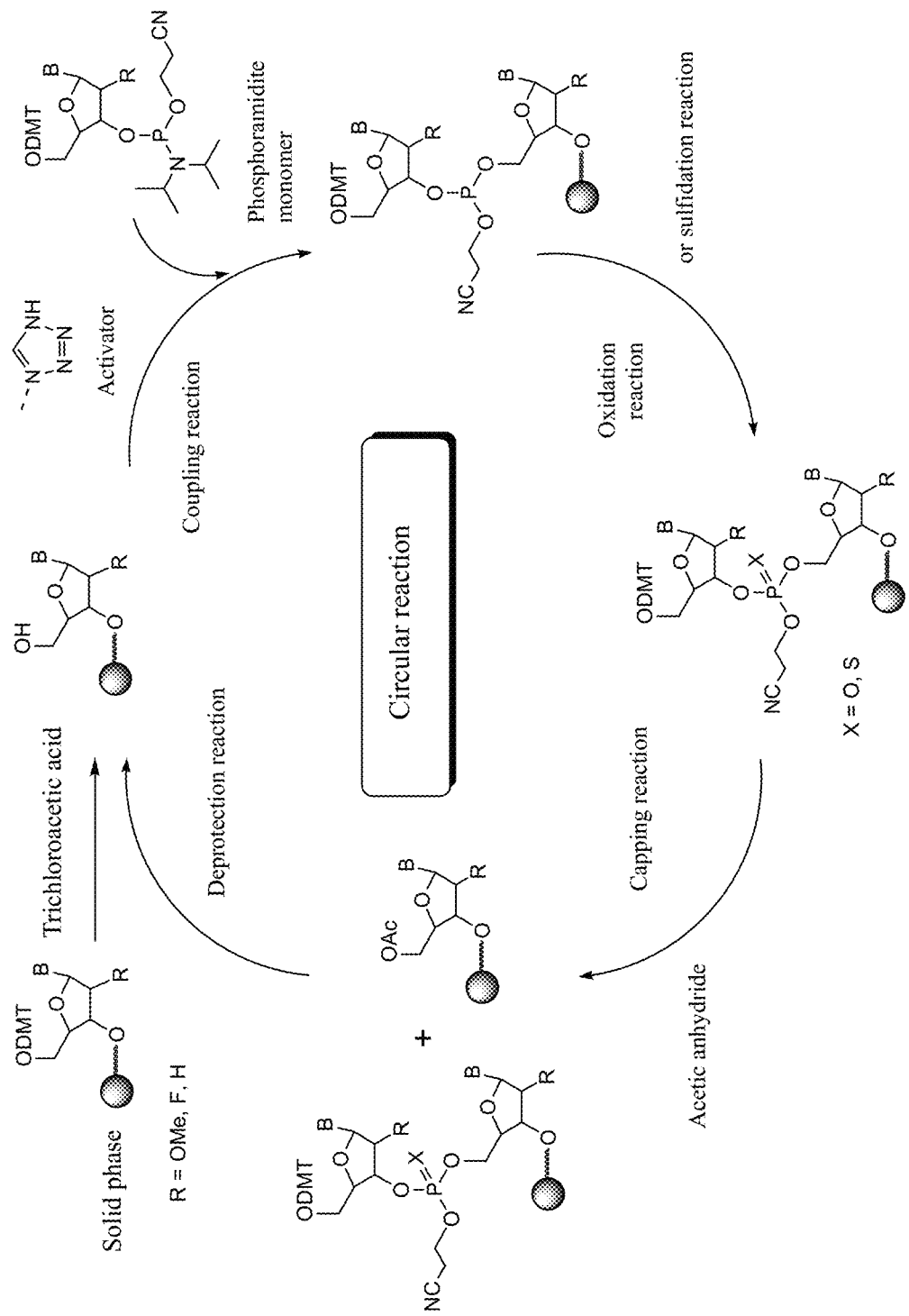
FIG. 1 illustrates a schematic diagram of the preparation process for a siRNA conjugate according to a specific embodiment of the present disclosure.

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values and the individual point value of the various ranges, and the individual point values may be combined with one another to produce one or more new numerical ranges, which should be deemed have been specifically disclosed herein.

In the present disclosure, the number of carbon atom(s) for C1-C10 group may be 1, 2, 3, 4, 5, 6, 7, 8, 9, or 10; the number of carbon atoms for C6-C10 group may be 6, 7, 8, 9, or 10; the number of carbon atoms for C5-C10 group may be 5, 6, 7, 8, 9, or 10.

In the present disclosure, the integers of 1-10 include 1, 2, 3, 4, 5, 6, 7, 8, 9 or 10; the integers of 1-4 include 1, 2, 3 or 4; the integers of 1-6 include 1, 2, 3, 4, 5 or 6.

In the present disclosure, Ac denotes acetyl.

In the present disclosure, Nu is an active drug, preferably a functional oligo-ribonucleic acid (oligo-RNA) and/or an oligo-deoxyribonucleic acid (oligo-DNA). In the present disclosure, the active drug Nu is preferably siRNA, such as the siRNA recited in the examples, and the conjugate according to the present disclosure may be connected with the 5' end or the 3' end of the sense strand of the siRNA via a phosphodiester bond, or connected with the 5' end or the 3' end of the antisense strand of the siRNA via a phosphodiester bond.

In a first aspect, the present disclosure provides a compound L2 with a structure represented by formula (I), (II), (III) or (IV):

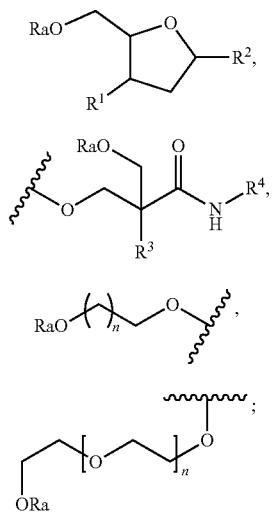

wherein the group Ra on formula (I), (II), (III) or (IV) is independently H or hydroxyl protecting group; the hydroxyl protecting group may be one selected from the group consisting of DMT (4,4'-dimethoxytrityl), MMT (4-methoxytrityl), trityl, TBDMS (t-butyldimethylsilyl), 4-oxopentanoyl, 2-cyanoethyl, PNT (4-pentenoyl) and acyloxyalkyl group;

$R^1$ and $R^2$ on formula (I) and $R^4$ on formula (II) each has a linking site of covalent bond;

n on formula (III) or (IV) is an integer of 1-10;

"~~~" on formula (II), (III) or (IV) denotes a structure obtained after linking with an active group via an active site; wherein the active site is a site connected via a covalent bond; and the active group is one selected from the group consisting of phosphoramidite group, H-phosphate group and polyhydroxyalkyl group.

$R^1$ and $R^2$ on formula (I) and $R^4$ on formula (II) are each independently a substituted or unsubstituted straight chain group having a length of C1-70, wherein one or more of the carbon atoms is optionally substituted by one or more selected from the group consisting of the following groups: C(O), NH, O and S; and wherein $R^1$ optionally have one or more substituents selected from the group consisting of the following groups: C1-C10 alkyl, C6-C10 aryl, C5-C10 heteroaryl, C1-C10 haloalkyl, —O(C1-C10 alkyl), —OC1-C10 (alkylphenyl), —C1-C10 alkyl-OH, —O—(C1-C10 haloalkyl), —S(C1-C10 alkyl), —S(C1-C10 alkylphenyl), —C1-C10 alkyl-SH, —S(C1-C10 haloalkyl), halogen substituent, —OH, —SH, —NH$_2$, —C1-C10 alkyl-NH$_2$, —N(C1-C10 alkyl) (C1-C10 alkyl), —NH(C1-C10 alkyl), cyano group, nitro, —CO$_2$H, —C(O)O(C1-C10 alkyl), —CON(C1-C10 alkyl) (C1-C10 alkyl), —CONH(C1-C10 alkyl), —CONH$_2$, —NHC(O)(C1-C10 alkyl), —NHC(O) (phenyl), —N(C1-C10 alkyl) C (O) (C1-C10 alkyl), —N(C1-C10 alkyl) C (O) (phenyl), —C(O) C1-C10 alkyl, —C(O)C1-C10 alkylphenyl, —OC(O)C1-C10 haloalkyl, —OC(O)C1-C10 alkyl, —SO$_2$ (C1-C10 alkyl), —SO$_2$ (phenyl), —SO$_2$ (C1-C10 haloalkyl), —SO$_2$NH$_2$, —SO$_2$NH(C1-C10 alkyl), —SO$_2$NH (phenyl), —NHSO$_2$ (C1-C10 alkyl), —NHSO$_2$ (phenyl) and —NHSO$_2$ (C1-C10 haloalkyl);

$R^2$ on formula (I) may also be H;

$R^3$ on formula (II) is a substituted or unsubstituted C1-C20 alkyl; and wherein $R^3$ may optionally have a substituent of any one or more of the group consisting of the following groups: C1-C10 alkyl, C6-C10 aryl, C5-C10 heteroaryl, C1-C10 haloalkyl, —OC1-C10 alkyl.

According to some embodiments of the present disclosure, $R^1$ is independently a group obtained by linking any number of one or more kinds of group selected from the following groups in a random manner:

—(CH$_2$)n-, —O— and —CONH—; wherein n is an integer of 1-10.

According to some embodiments of the present disclosure, $R^2$ and $R^4$ are each independently a group obtained by linking any number of one or more kinds of group selected from the following groups in a random manner:

—(CH$_2$)n-, —O—, —CONH— and —(OCH$_2$CH$_2$)n-; wherein n is an integer of 1-10.

According to some embodiments of the present disclosure, $R^3$ is a C1-C6 alkyl.

According to some embodiments of the present disclosure, the compound L2 has one of structures represented by formulae (A1)-(A24):

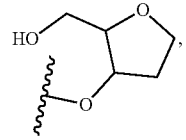

(A1)

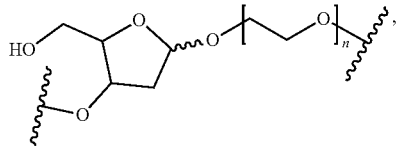

(A2)

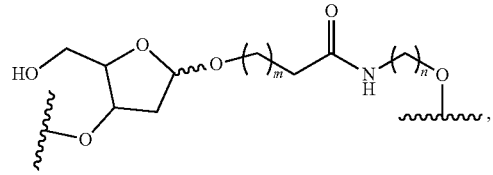

(A3)

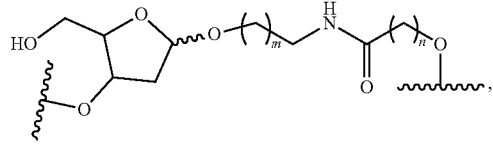

(A4)

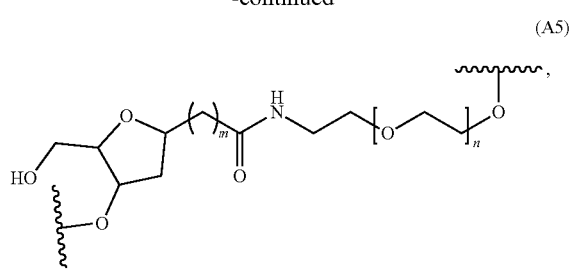
(A5)
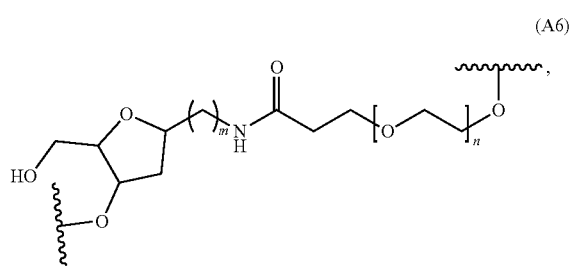
(A6)
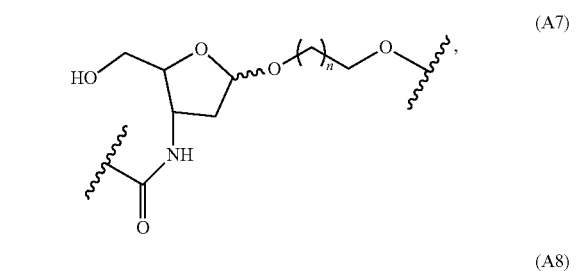
(A7)
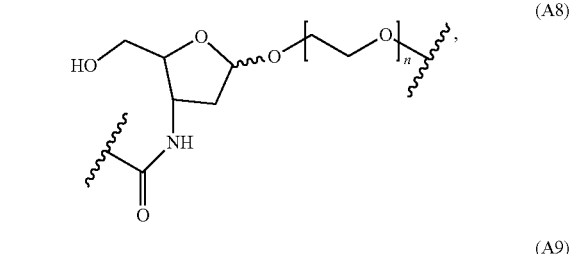
(A8)
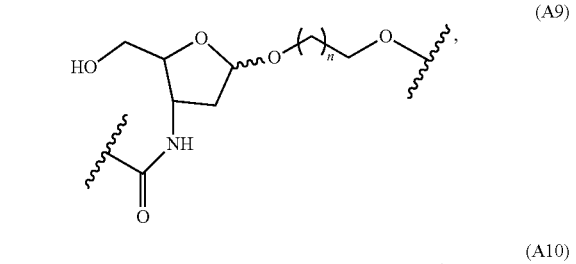
(A9)
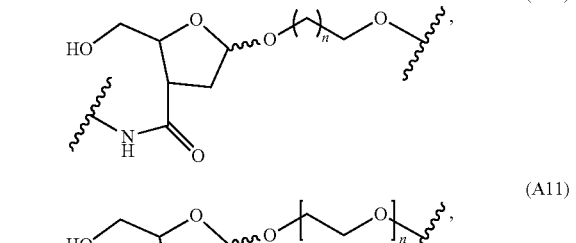
(A10)
(A11)
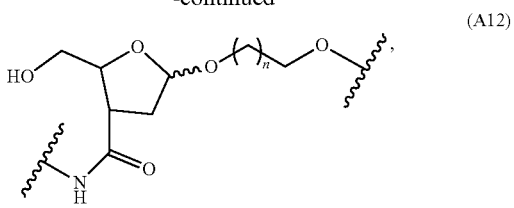
(A12)
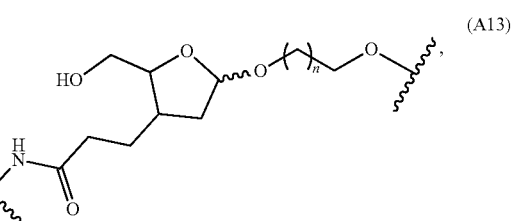
(A13)
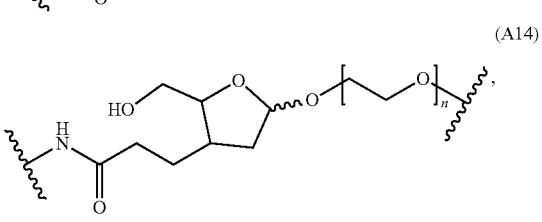
(A14)
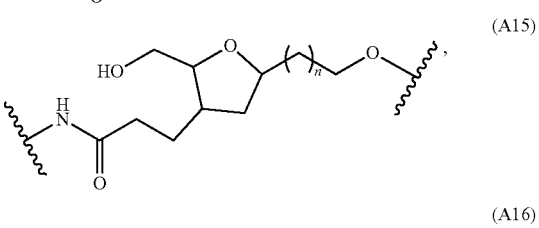
(A15)
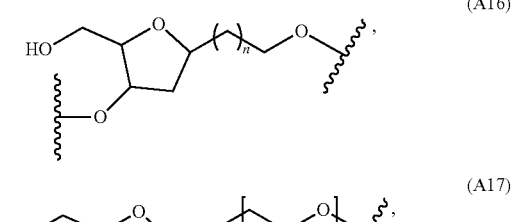
(A16)
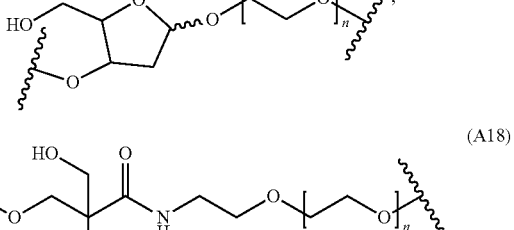
(A17)
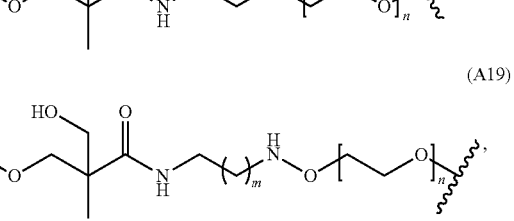
(A18)
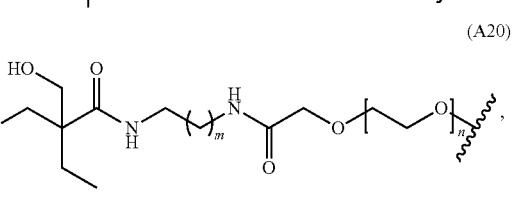
(A19)
(A20)

-continued

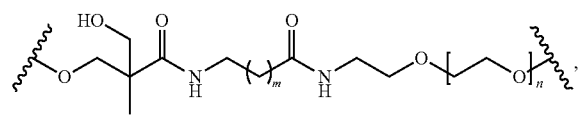
(A21)

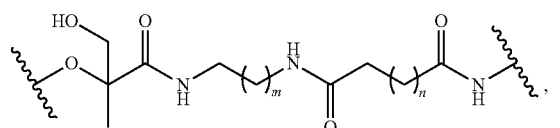
(A22)

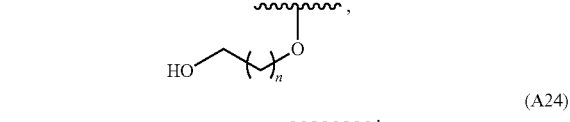
(A23)

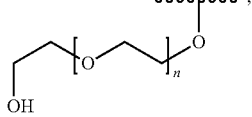
(A24)

wherein m or n on formulae (A2)-(A24) is independently an integer of 1-10; "~~~" denotes a structure obtained after linking with an active group via an active site; wherein the active site is a site connected via a covalent bond; and the active group is one selected from the group consisting of phosphoramidite group, H-phosphate group, phosphate group and polyhydroxyalkyl group.

According to some embodiments of the present disclosure, —OH on formulae (A2)-(A24) denotes hydroxyl group or hydroxyl group protected by a hydroxyl protecting group, wherein the hydroxyl protecting group is one selected from the group consisting of DMT (4,4'-dimethoxytrityl), MMT (4-methoxytrityl), trityl, TBDMS (t-butyldimethylsilyl), 4-oxopentanoyl, 2-cyanoethyl, PNT (4-pentenoyl) and acyloxyalkyl group.

Figure 4A:
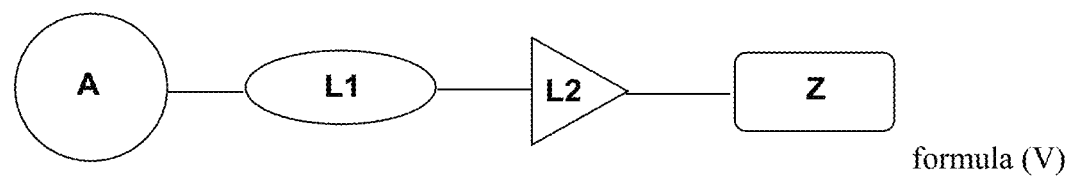
FIG. 4A and FIG. 4B are schematics of an aspect of the present disclosure depicting a compound M with a structure represented by formula (V) or (V').
Figure 4B:
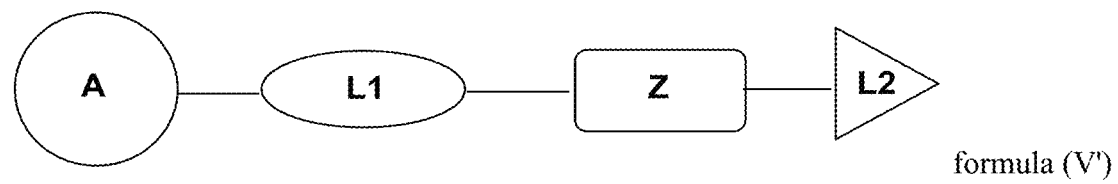

A second aspect of the present disclosure provides a compound M with a structure represented by formula (V) or (V') as shown in FIG. 4A and FIG. 4B, In formula (V) or (V'), A denotes an aptamer with a structure derived from a saccharide or a polypeptide, which is the structure that promotes binding between the delivered substance and the corresponding ligand (e.g., asialoglycoprotein receptor) with the high affinity and strong specificity;

L1 is a straight chain group containing an ether linkage and/or an amide linkage having a length of C1-50;

the structure of L2 is as previously described (the site of linking L2 with A, L1 and Z may be on O, S, N, C);

Z has a structure which is derived from a first phosphorus-containing compound and mainly plays a linking and coupling role, the first phosphorus-containing compound may be one selected from phosphoramidite, H-phosphate and phosphotriester, and is capable of covalently linking to adjacent groups via phosphate ester bond or a phosphamide diester bond.

According to some embodiments of the present disclosure, L1 may be a group obtained by linking any number of one or more kinds of group selected from the following groups in a random manner:

—CH$_2$—, —O—, —OCH$_2$— and —CONH—.

According to some embodiments of the present disclosure, L1 may be one selected from the group consisting of the following groups:

—O—[CH$_2$CH$_2$O]—$_n$, —[CH$_2$]$_m$—CONH—[CH$_2$]$_n$O— and —O—[CH$_2$CH$_2$O]$_m$—CONH—[CH$_2$]$_n$O—;

wherein m and n are each independently an integer of 1-10.

According to some embodiments of the present disclosure, the saccharide may be one selected from the group consisting of a monosaccharide, a disaccharide, a trisaccharide or a polysaccharide; preferably, the saccharide may be a modified saccharide.

According to some embodiments of the present disclosure, A may be one selected from the group consisting of D-mannopyranose, L-mannopyranose, D-arabinose, D-xylofuranose, L-xylofuranose, D-glucose, L-glucose, D-galactose, L-galactose, α-D-mannopyranose, β-D-mannopyranose, α-D-glucopyranose, β-D-glucopyranose, α-D-glucofuranos, β-D-glucofuranose, α-D-fructofuranose, α-D-fructopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-butyrylgalactosamine, N-isobutyrylgalactosamine, 2-amino-3-O—[(R)-L-carboxyethyl]-2-deoxy-β-D-glucopyranose, 2-deoxy-2-methylamino-L-glucopyranose, 4,6-dideoxy-4-carboxamido-2,3-di-O-methyl-D-mannopyranose, 2-deoxy-2-sulfono-D-glucopyranose, N-glycoloyl-α-neuraminic acid, 5-thio-β-D-glucopyranose, 2,3,4-tri-O-acetyl-L-thio-6-O-trityl-α-D-glucopyranoside methyl ester, 4-thio-β-D-galactopyranose, 3,4,6,7-tetra-O-acetyl-2-deoxy-1,5-dithio-α-D-glucoheptopyranoside ethyl ester, 2,5-anhydro-D-psicose nitrile, ribose, D-4-thioribose, L-ribose or L-4-thioribose; preferably, the saccharide is N-acetylgalactosamine (GalNAc).

According to some embodiments of the present disclosure, A can also be one selected from the group consisting of a protein, a monoclonal antibody and a nanobody.

In the present disclosure, A may be selected from the group consisting of ligands capable of binding with a receptor on the surface of a cell; and A has an active hydroxyl group or an amino group, and A may be covalently linked to L1 via the hydroxyl group or amino group, and the function of A is to deliver an active drug Nu to the target site by virtue of its affinity with the receptor; when A is a saccharide, the linking site typically includes the 1-site hydroxyl group.

In the present disclosure, the receptor may be a hepatocyte surface receptor, or an asialoglycoprotein receptor on human hepatocytes.

In the present disclosure, the active drug Nu may be an oligo-ribonucleic acid and/or an oligo-deoxyribonucleic acid.

According to some embodiments of the present disclosure, Z has a structure represented by formula (B1), (B2), (B3), (B4), (B5) or (B6):

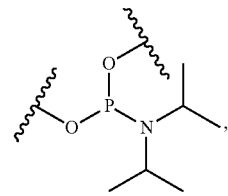
(B1)

(B2)
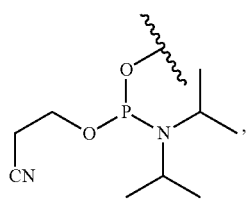

(B3)
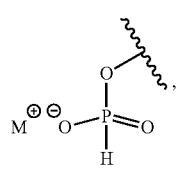

(B4)
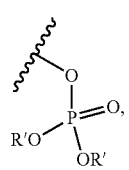

(B5)
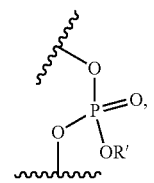

(B6)
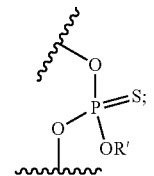

wherein, M on formula (B3) is one selected from the group consisting of TEA (triethylamine), trimethylamine, triisopropylamine and tripropylamine. Wherein R' on formulae (B4)-(B6) can be one selected from the group consisting of 2,2,2-trichloroethyl, phenyl, o-chlorophenyl, cyanoethyl, and Nu. "~~~~" in (B1), (B2), (B3), (B4), (B5), or (B6) denotes a site which can be linked by a covalent bond.

According to some embodiments of the present disclosure, the compound M has a structure represented by formula (101), (102), (201), (202), (203), (301) or (302):

(101)
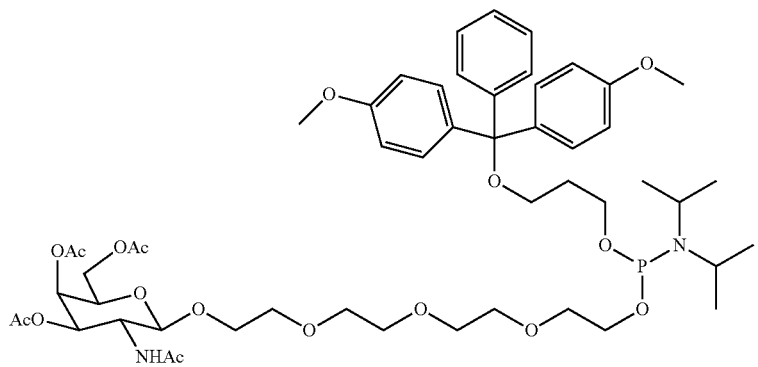

(102)
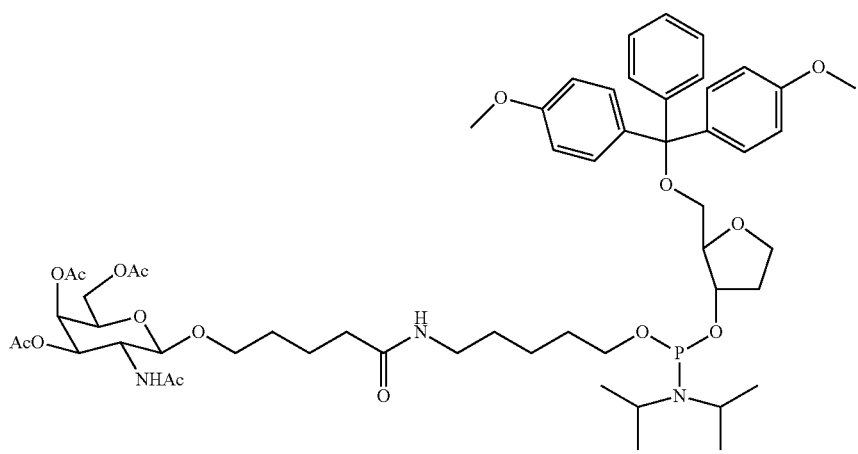

(201)
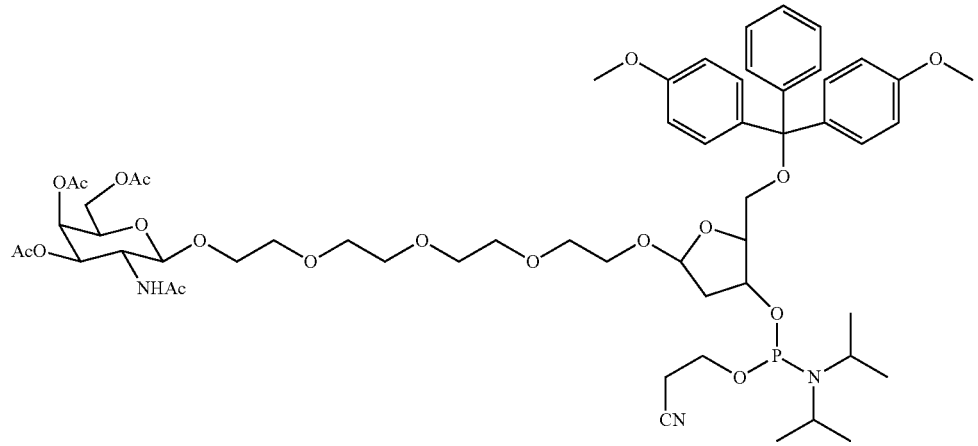
(202)
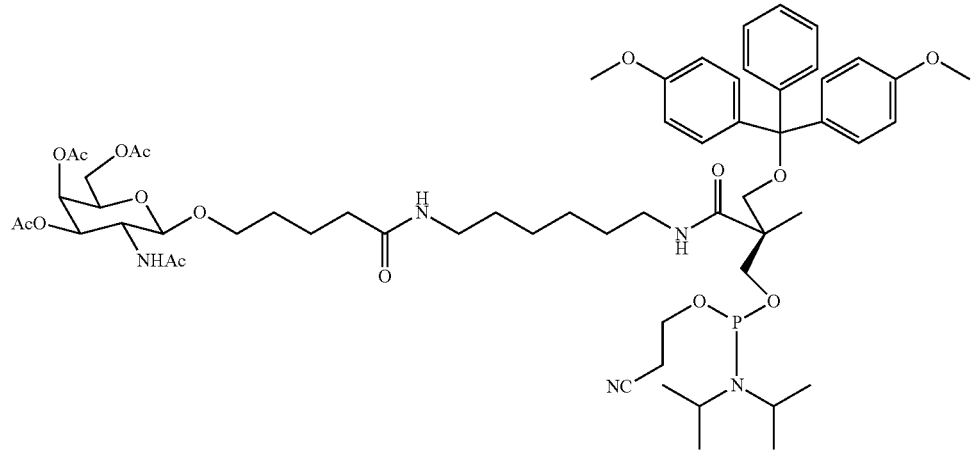
(203)
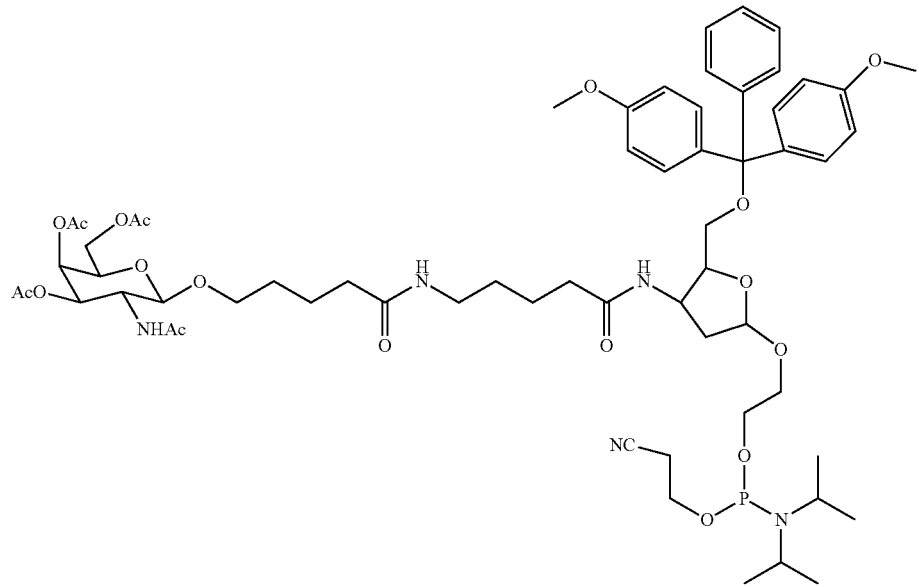

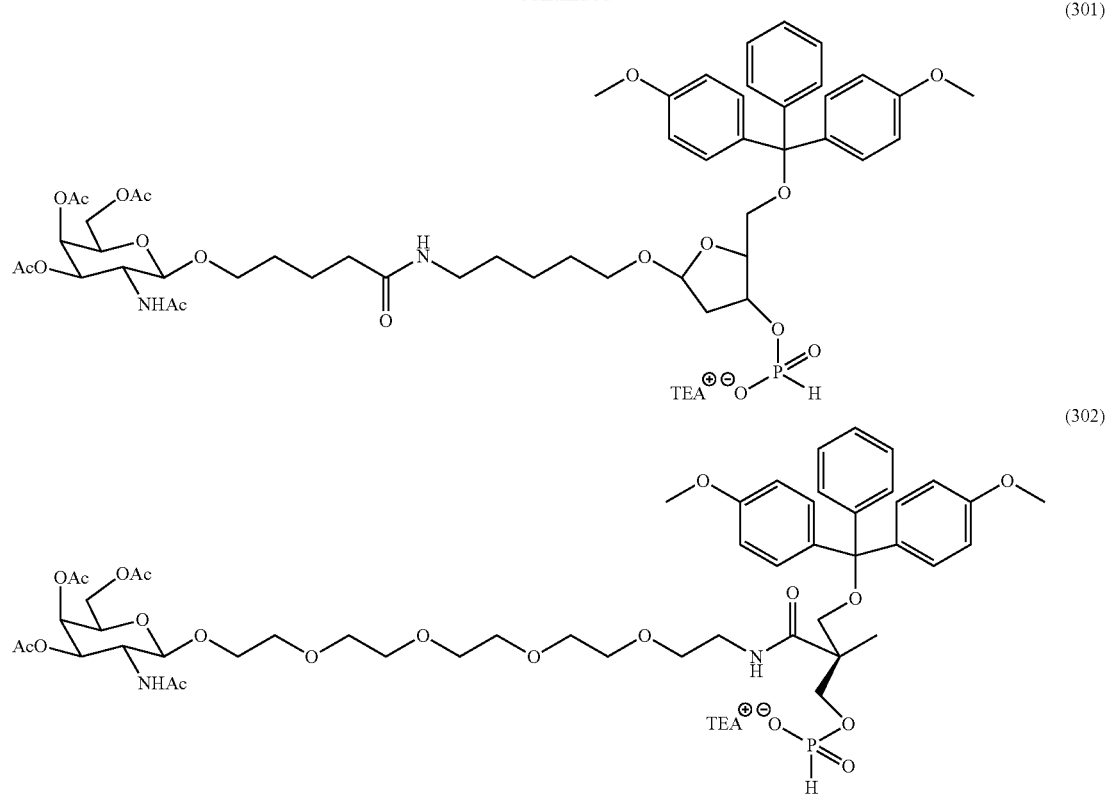

According to some embodiments of the present disclosure, the compound M may be linked with an active drug Nu; the active drug Nu may be linked with the compound M via a phosphate bond (e.g., a phosphodiester bond or a phosphorothioate diester bond) or a phosphamide diester bond. The active drug Nu is as previously mentioned.

A third aspect the present disclosure provides a first conjugate N having the structure shown in formula (VI):

(M)m-R''      (VI)

m on formula (VI) may be an integer of 1-4, when m is greater than 1, M may independently be of a structure shown in formula (V) or (V'), and each M may be the same or different; R'' has an active site capable of being linked with the active drug Nu; or R'' may be a group linked with the active drug Nu via an active site.

According to some embodiments of the present disclosure, the first conjugate N has a structure represented by formula (a), (b), (c), (d) or (e):

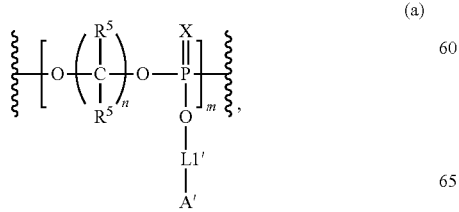

(a)

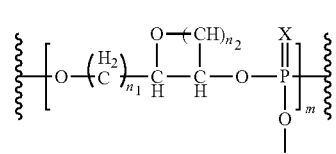

(b)

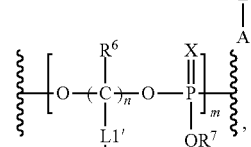

(c)

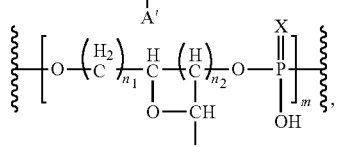

(d)

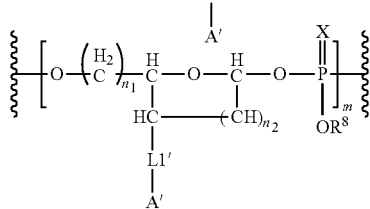

(e)

wherein in formulae (a), (b), (c), (d) or (e),
n, n1 or n2 each is independently an integer of 1-10, preferably an integer of 1-6; m is independently an integer of 1-10, preferably an integer of 1-4; X denotes O or S;

L1' is a straight chain group containing an ether linkage and/or an amide linkage having a length of C1-50;

A' denotes an aptamer with a structure derived from saccharide or polypeptide, A is a structure that can promote binding of the delivered substance to the corresponding ligand (e.g., the asialoglycoprotein receptor) with high affinity and strong specificity;

$R^5$ on formula (a) is each independently selected from H, C1-C10 alkyl, C1-C10 haloalkyl or C1-C10 alkoxy;

$R^6$ on formula (C) is selected from H, C1-C10 alkyl, C1-C10 haloalkyl or C1-C10 alkoxy; and $R^7$ is H or a hydroxyl protecting group, wherein the hydroxyl protecting group is one selected from the group consisting of DMT (4,4'-dimethoxytrityl), MMT (4-methoxytrityl), trityl, TBDMS (t-butyldimethylsilyl), 4-oxopentanoyl, 2-cyanoethyl, PNT (4-pentenoyl) and acyloxyalkyl, preferably, $R^7$ is 2-cyanoethyl;

$R^8$ on formula (e) is H or a hydroxyl protecting group; wherein the hydroxyl protecting group is one selected from the group consisting of DMT (4,4'-dimethoxytrityl), MMT (4-methoxytrityl), trityl, TBDMS (t-butyldimethylsilyl), 4-oxopentanoyl, 2-cyanoethyl, PNT (4-pentenoyl) and acyloxyalkyl, preferably, $R^8$ is 2-cyanoethyl;

where "〜〜〜" may denote a site linked to an active drug Nu or other group via a covalent bond, or "〜〜〜" may denote a group linked with an active drug Nu via a covalent bond. The active drug Nu is as previously mentioned.

According to some embodiments of the present disclosure, L1' may be a group obtained by linking any number of one or more kinds of group selected from the following groups in a random manner:

—CH$_2$—, —O—, —OCH$_2$— and —CONH—.

According to some embodiments of the present disclosure, L1' may be one selected from the group consisting of the following groups:

—O—[CH$_2$CH$_2$O]—$_n$, —[CH$_2$]$_m$—CONH—[CH$_2$]$_n$O— and —O—[CH$_2$CH$_2$O]$_m$—CONH—[CH$_2$]$_n$O—; wherein m and n are each independently an integer of 1-10.

According to some embodiments of the present disclosure, A' may be one selected from the group consisting of a monosaccharide, a disaccharide, a trisaccharide or a polysaccharide; and A' may be a modified saccharide.

According to some embodiments of the present disclosure, A' may be one selected from the group consisting of D-mannopyranose, L-mannopyranose, D-arabinose, D-xylofuranose, L-xylofuranose, D-glucose, L-glucose, D-galactose, L-galactose, α-D-mannopyranose, β-D-mannopyranose, α-D-glucopyranose, β-D-glucopyranose, α-D-glucofuranose, β-D-glucofuranose, α-D-fructofuranose, α-D-fructopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-butyrylgalactosamine, N-isobutyrylgalactosamine, 2-amino-3-O—[(R)-L-carboxyethyl]-2-deoxy-β-D-glucopyranose, 2-deoxy-2-methylamino-L-glucopyranose, 4,6-dideoxy-4-carboxamido-2,3-di-O-methyl-D-mannopyranose, 2-deoxy-2-sulfono-D-glucopyranose, N-glycoloyl-α-neuraminic acid, 5-thio-β-D-glucopyranose, 2,3,4-tri-O-acetyl-L-thio-6-O-trityl-α-D-glucopyranoside methyl ester, 4-thio-β-D-galactopyranose, 3,4,6,7-tetra-O-acetyl-2-deoxy-1,5-dithio-α-D-glucoheptopyranoside ethyl ester, 2,5-anhydro-D-psicose nitrile, ribose, D-4-thioribose, L-ribose or L-4-thioribose; preferably, A' is N-acetylgalactosamine (GalNAc).

According to some embodiments of the present disclosure, A' can further be one selected from the group consisting of a protein, a monoclonal antibody and a nanobody.

In the present disclosure, A' may be selected from the group consisting of ligands capable of binding with a receptor on the surface of a cell; and A' has an active hydroxyl group or an amino group, and A' may be covalently linked to L1 via hydroxyl group or amino group, and the function of A' include to deliver an active drug Nu to the target site by virtue of its affinity with the receptor; when A' is a saccharide, the linking site typically includes the 1-site hydroxyl group.

According to some embodiments of the present disclosure, the first conjugate N has a structure represented by formula (401), (402), (501), (502) or (503):

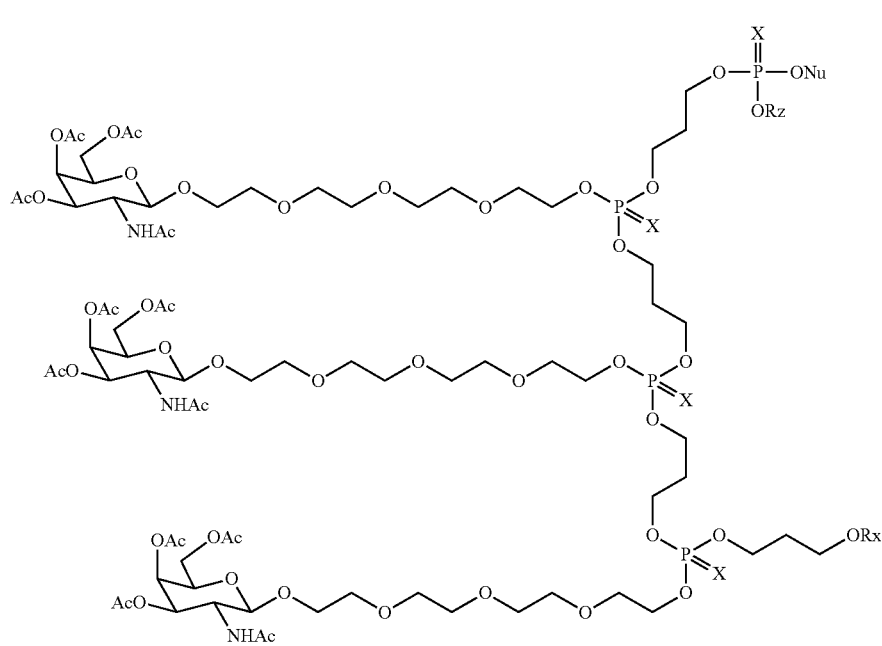

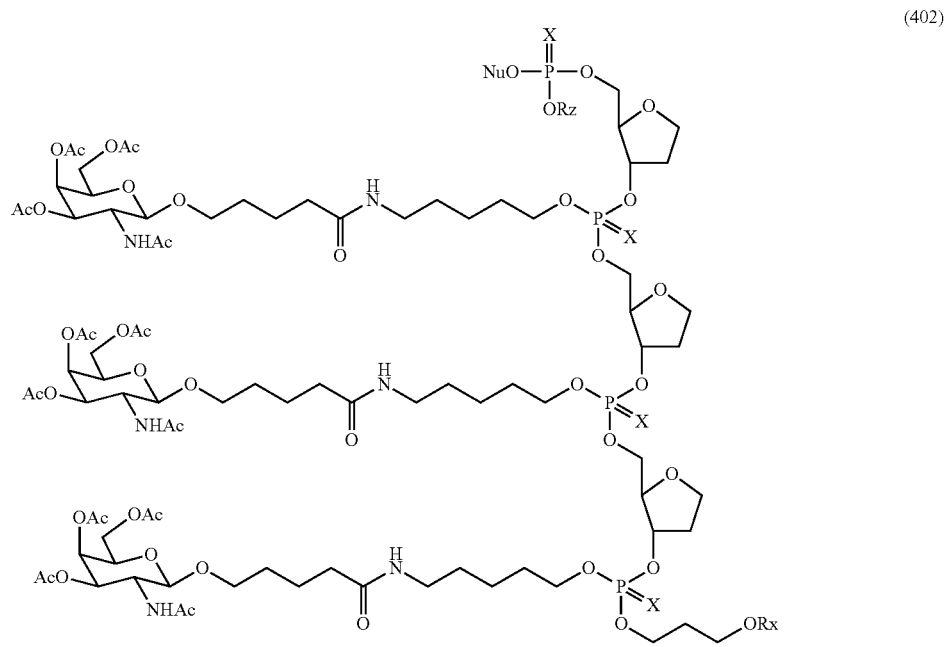
(402)
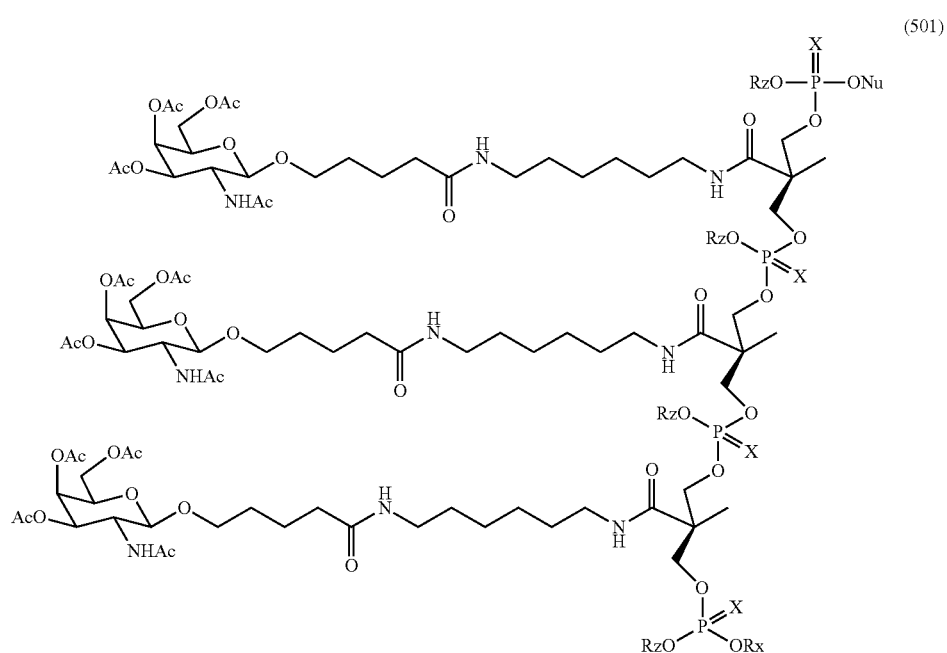
(501)

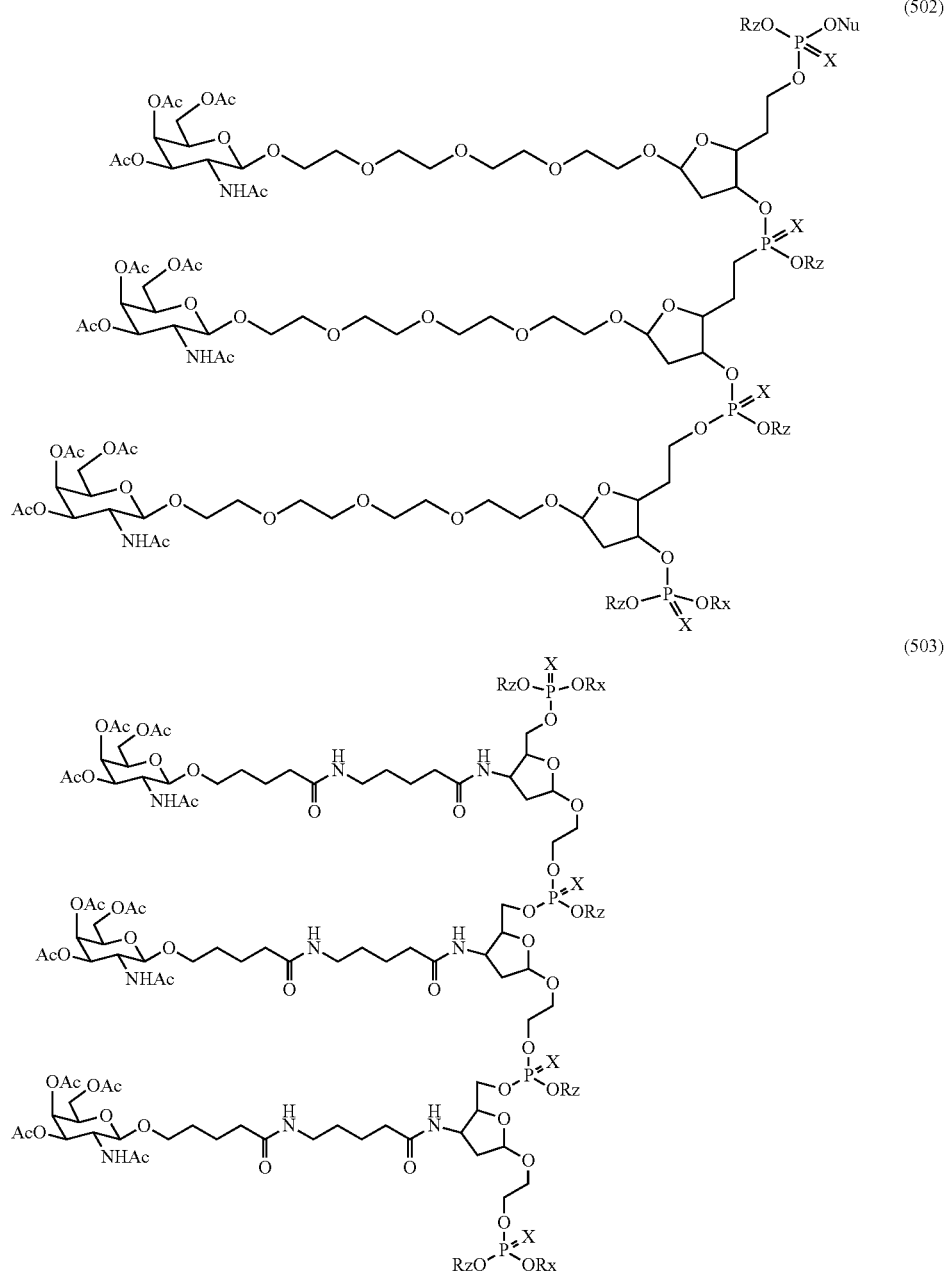

In formulae (401), (402), (501), (502) or (503), X is O or S; Rx has a site group linked with a solid phase carrier, and optionally a succinamide group or a hydroxyl group on the solid phase carrier; Nu is an active drug small nucleic acid (e.g., an active functional oligonucleotide) linked via a covalent bond; and Rz is a hydroxyl protecting group, it may be selected from 2-cyanoethyl.

According to some embodiments of the present disclosure, Nu on formula (401), (402), (501), (502) or (503) may be substituted by other groups having an active site.

A fourth aspect of the present disclosure provides a compound L3 having the structure represented by formula (VII):

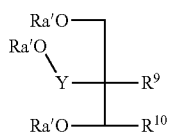

Wherein Y is a substituted or unsubstituted straight chain group having a length of C1-10, wherein one or more carbon atoms are optionally substituted by one or more —CONH—;

Ra' on formula (VII) is each independently H or a hydroxyl protecting group; the hydroxyl protecting group may be one selected from the group consisting of DMT (4,4'-dimethoxytrityl), MMT (4-methoxytrityl), trityl, TBDMS (t-butyldimethylsilyl), 4-oxopentanoyl, 2-cyanoethyl, PNT (4-pentenoyl) and acyloxyalkyl;

$R^9$ and $R^{10}$ are each independently H, or a straight chain group having a length of C1-70 and having a terminal group containing hydroxyl group and/or hydroxyl group protected by hydroxyl protecting group, wherein one or more carbon atoms are optionally substituted by one or more selected from the group consisting of the following groups: C (O), NH, O and S; and wherein $R^9$ and $R^{10}$ independently and optionally have one or more substituents selected from the group consisting of the following groups: C1-C10 alkyl, C6-C10 aryl, C5-C10 heteroaryl, C1-C10 haloalkyl, —O(C1-C10 alkyl), —O(C1-C10 alkylphenyl), —C1-C10 alkyl-OH, —O(C1-C10 haloalkyl), —S(C1-C10 alkyl), —S(C1-C10 alkylphenyl), —C1-C10 alkyl-SH, —S(C1-C10 haloalkyl), halogen substituent, —OH, —SH, —NH$_2$, —C1-C10 alkyl-NH$_2$, —N(C1-C10 alkyl) (C1-C10 alkyl), —NH(C1-C10 alkyl), cyano group, nitro, —CO$_2$H, —C(O) O(C1-C10 alkyl), —CON(C1-C10 alkyl) (C1-C10 alkyl), —CONH(C1-C10 alkyl), —CONH$_2$, —NHC(O)(C1-C10 alkyl), —NHC(O) (phenyl), —N(C1-C10 alkyl) C (O) (C1-C10 alkyl), —N(C1-C10 alkyl) C (O) (phenyl), —C(O)C1-C10 alkyl, —C(O) C1-C10 alkylphenyl, —OC(O)C1-C10 haloalkyl, —OC(O)C1-C10 alkyl, —SO$_2$ (C1-C10 alkyl), —SO$_2$ (phenyl), —SO$_2$ (C1-C10 haloalkyl), —SO$_2$NH$_2$, —SO$_2$NH(C1-C10 alkyl), —SO$_2$NH (phenyl), —NHSO$_2$ (C1-C10 alkyl), —NHSO$_2$ (phenyl) and —NHSO$_2$ (C1-C10 haloalkyl). Wherein $R^9$ and $R^{10}$ may further represent a group having a site for linking with an active drug Nu. The active drug Nu is as previously mentioned.

According to some embodiments of the present disclosure, Y may be —CONH— or CH$_2$.

According to some embodiments of the present disclosure, $R^9$ and $R^{10}$ are each independently a group obtained by linking any number of one or more kinds of group selected from the following groups in a random manner:

—NH$_2$—, —CH$_2$—, —O—, —CONH—, —(OCH$_2$CH$_2$)n-, Z',

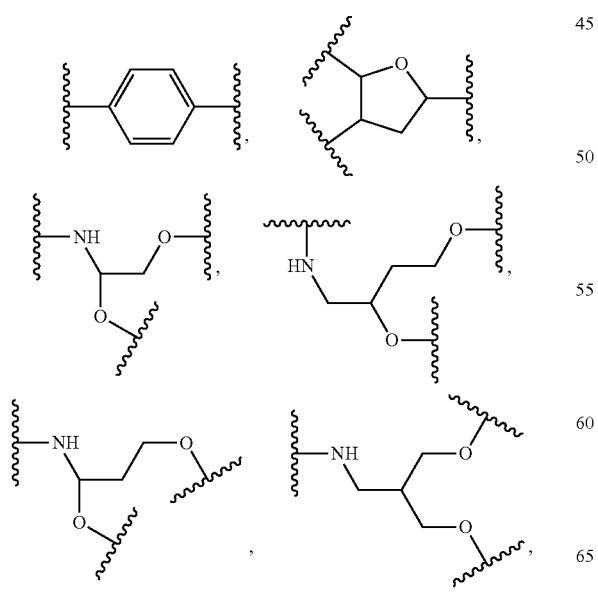

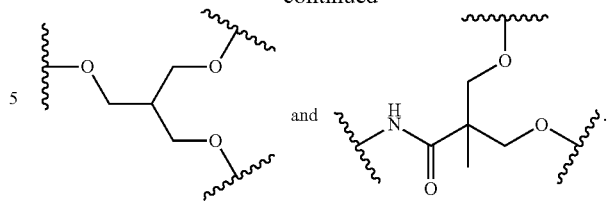

In the present disclosure,

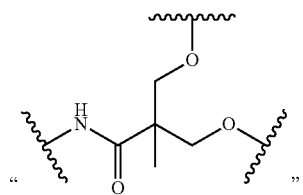 [SMILES: *NC(=O)C(C)(CO*)CO*]

can be derived from a group represented by formula (F1), formula (F2), formula (F3) or formula (F4),

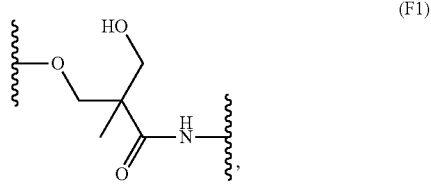

(F1)

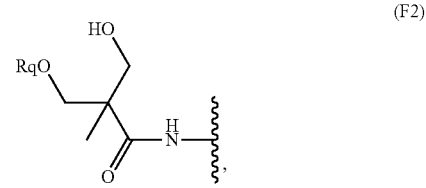

(F2)

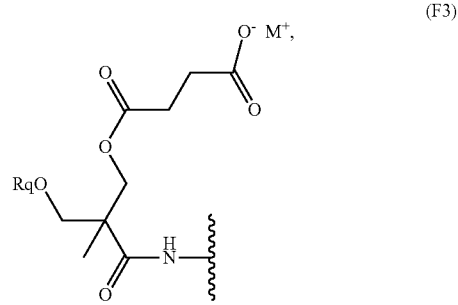

(F3)

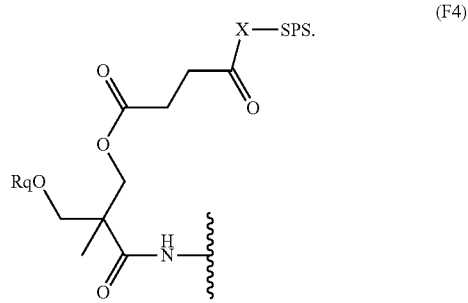

(F4)

Rq on formula (F1), formula (F2), formula (F3) or formula (F4) is a hydroxyl protecting group, and Rq may be one selected from the group consisting of trityl, 4-methoxytrityl, 4,4'-dimethoxytrityl and 4,4',4"-trimethoxybenzyl. In formula (F3), M⁺ can be a cation or a metal cation, and preferably, M⁺ is selected from primary amine cations, tertiary amine cations and quaternary amine cations. In formula (F4), X is O or NH, and SPS denotes a solid phase carrier.

According to some embodiments of the present disclosure, $R^9$ and $R^{10}$ each independently has a structure represented by formula (D1), (D2) or (D3):

wherein, Q and Q' are each independently O or S; $R^{11}$ and $R^{12}$ are each independently selected from the group consisting of H, C1-C10 alkyl, C1-C10 haloalkyl or C1-C10 alkoxy; and wherein $R^{11}$ and $R^{12}$ each independently comprises one or more of the following groups: nitrile group, amino group, hydroxyl group, carboxyl group and amide group.

According to some embodiments of the present disclosure, compound L3 has a structure represented by any one of formulae (E1)-(E12):

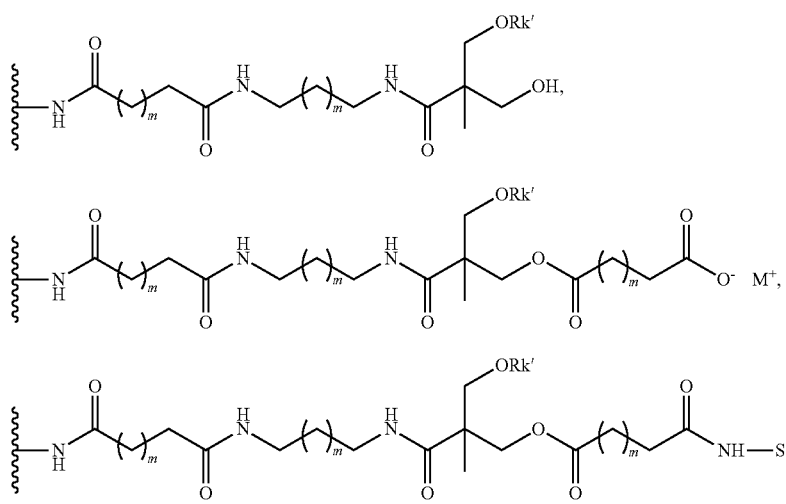

wherein m is an integer of 0-6 (e.g., 0, 1, 2, 3, 4, 5, 6); and M⁺ is triethylamine cation.

$R_{k'}$ is independently selected from H, hydroxyl protecting group or Nu; the hydroxyl protecting group is one selected from the group consisting of 4,4'-dimethoxytrityl, 4-methoxytrityl, trityl, t-butyldimethylsilyl, 4-oxopentanoyl, 2-cyanoethyl, 4-pentenoyl and acyloxyalkyl group; Nu is an active drug. $R_{k'}$ can also denote a site linked with an active drug Nu. $R_{k'}$ can further denote a group linked with an active drug Nu via an active site.

Wherein n is an integer of 1-10; Z' is a second phosphorus-containing compound and may link with other groups via a phosphate or phosphoramidite diester bond by a covalent bond.

According to some embodiments of the present disclosure, Z' has a structure represented by formula (C1) or (C2):

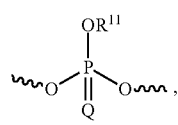

(C1)

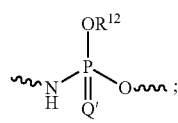

(C2)

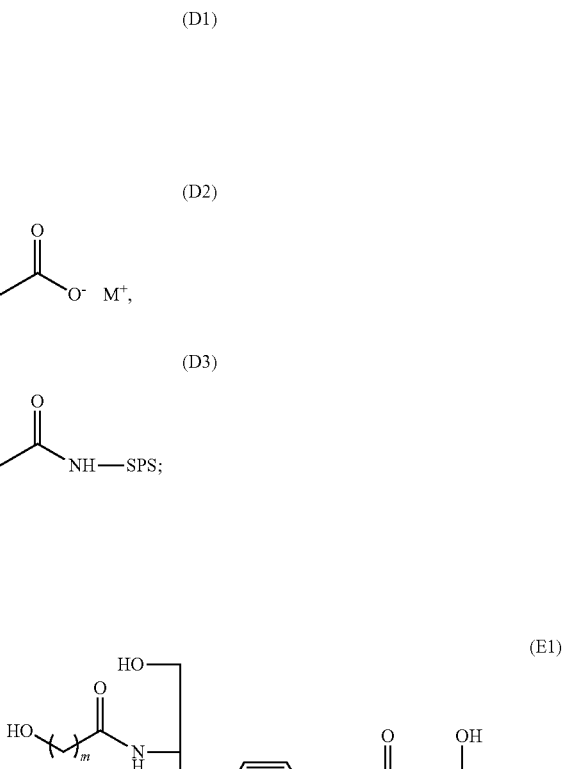

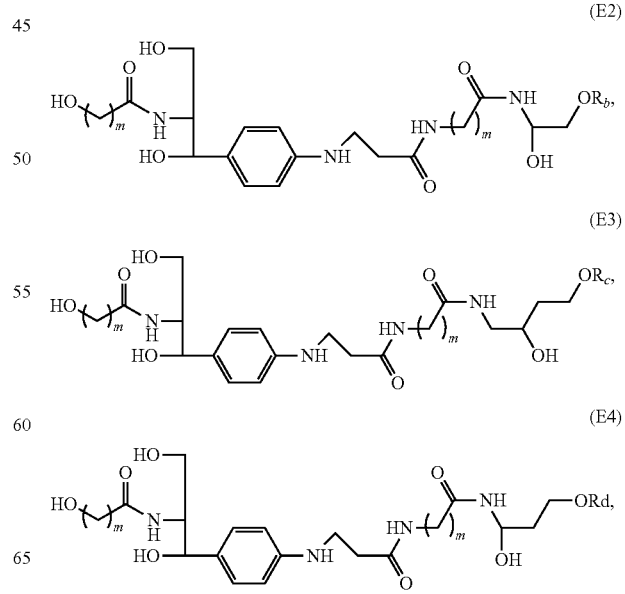

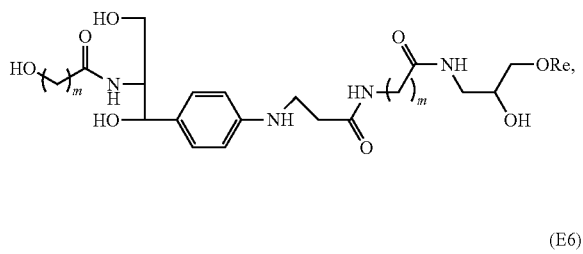
(E5)

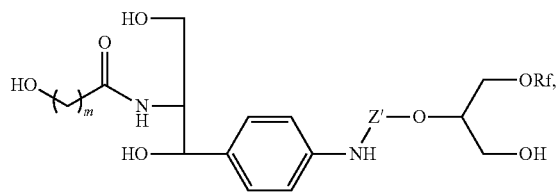
(E6)

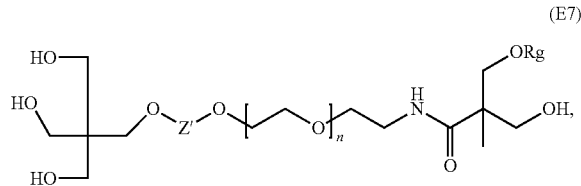
(E7)

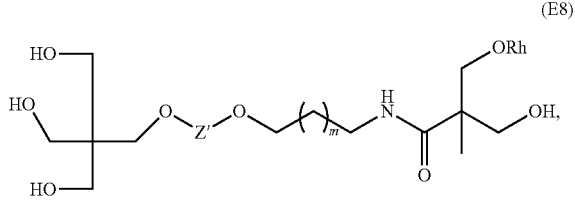
(E8)

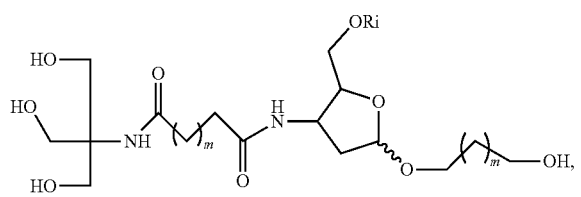
(E9)

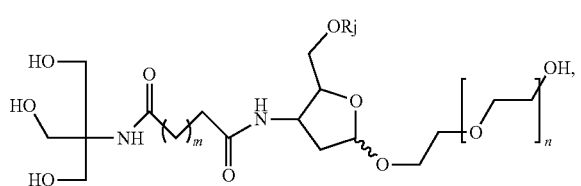
(E10)

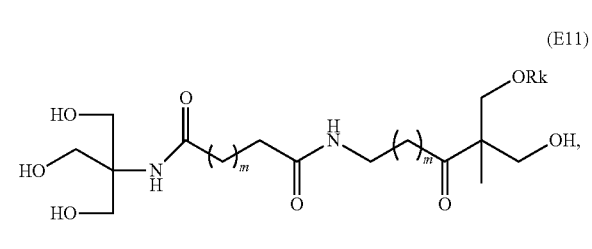
(E11)

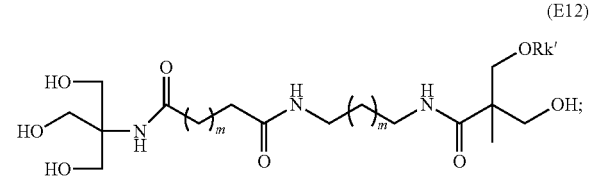
(E12)

wherein m and n on formulae (E1)-(E12) are each independently an integer of 1-10; $R_b$—$R_k$ and $R_{k'}$ are each independently selected from H, hydroxyl protecting group or Nu, wherein the hydroxyl protecting group is one selected from the group consisting of DMT (4,4'-dimethoxytrityl), MMT (4-methoxytrityl), trityl, TBDMS (t-butyldimethylsilyl), 4-oxopentanoyl, 2-cyanoethyl, PNT (4-pentenoyl) and acyloxyalkyl.

Figure 5:
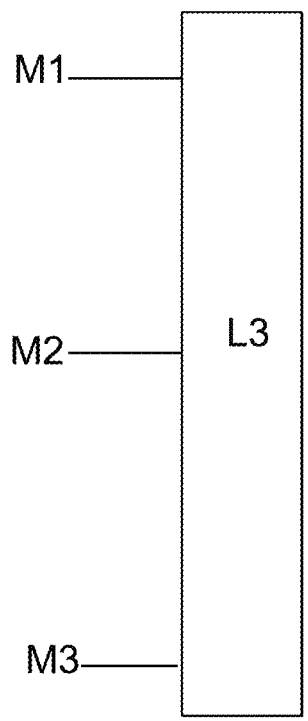
FIG. 5 is a schematic of another aspect of the present disclosure depicting a conjugate T with a structure of formula (VIII).

A fifth aspect the present disclosure provides a second conjugate T with a structure shown in formula (VIII) as shown in FIG. 5.

at least one of M1, M2, and M3 on formula (VIII) has a structure derived from the aforementioned compound M, wherein the structure of the compound M is as previously described, or each of M1, M2 and M3 is independently obtained by linking any number of A, L1, L2 or Z as defined above in a random manner. The compound shown in formula (VIII) may also be the one linked with an active drug Nu; the active drug Nu is as previously described.

According to some embodiments of the present disclosure, M1, M2 and M3 are the same or different.

According to some embodiments of the present disclosure, M1, M2 and M3 each has a structure derived from the aforementioned compound M, the structures are the same or different.

Figure 6A:
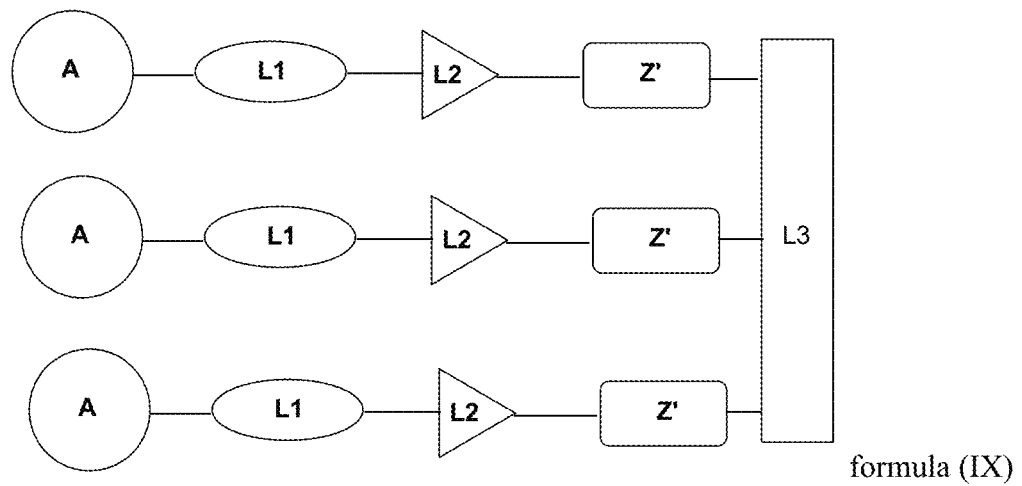
FIG. 6A and FIG. 6B are schematics of some embodiments of the present disclosure, wherein the second conjugate T has a structure represented by formula (IX) or formula (X).
Figure 6B:
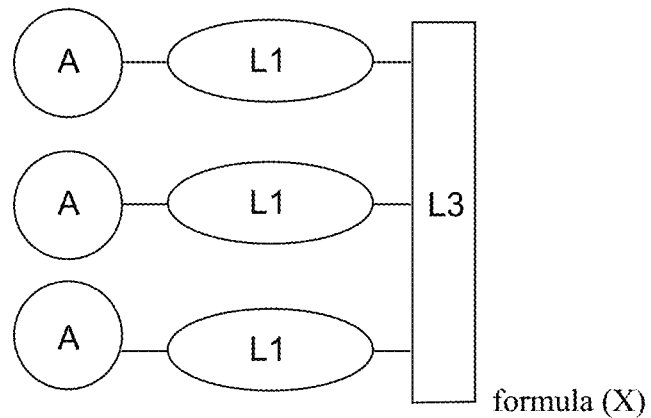

According to some embodiments of the present disclosure, the second conjugate T has a structure represented by formula (IX) or formula (X) as shown in FIG. 6A and FIG. 6B.

In formula (IX), the structure of A, L1, L2, L3 or Z' is as previously mentioned; wherein Z' may be a structure that is formed after linking Z with L3. In formula (X), the structure of A and L1 is as previously described. Wherein the compound represented by formula (IX) and formula (X) can also be the one linked with an active drug Nu, Nu may further refer to a protecting group or a solid phase carrier. The protecting group is as previously described. The kind of the solid phase carrier is not particularly limited, it may be a conventional choice in the art.

According to some embodiments of the present disclosure, the conjugate T has a structure shown by formula (IX-1) or formula (X-1):

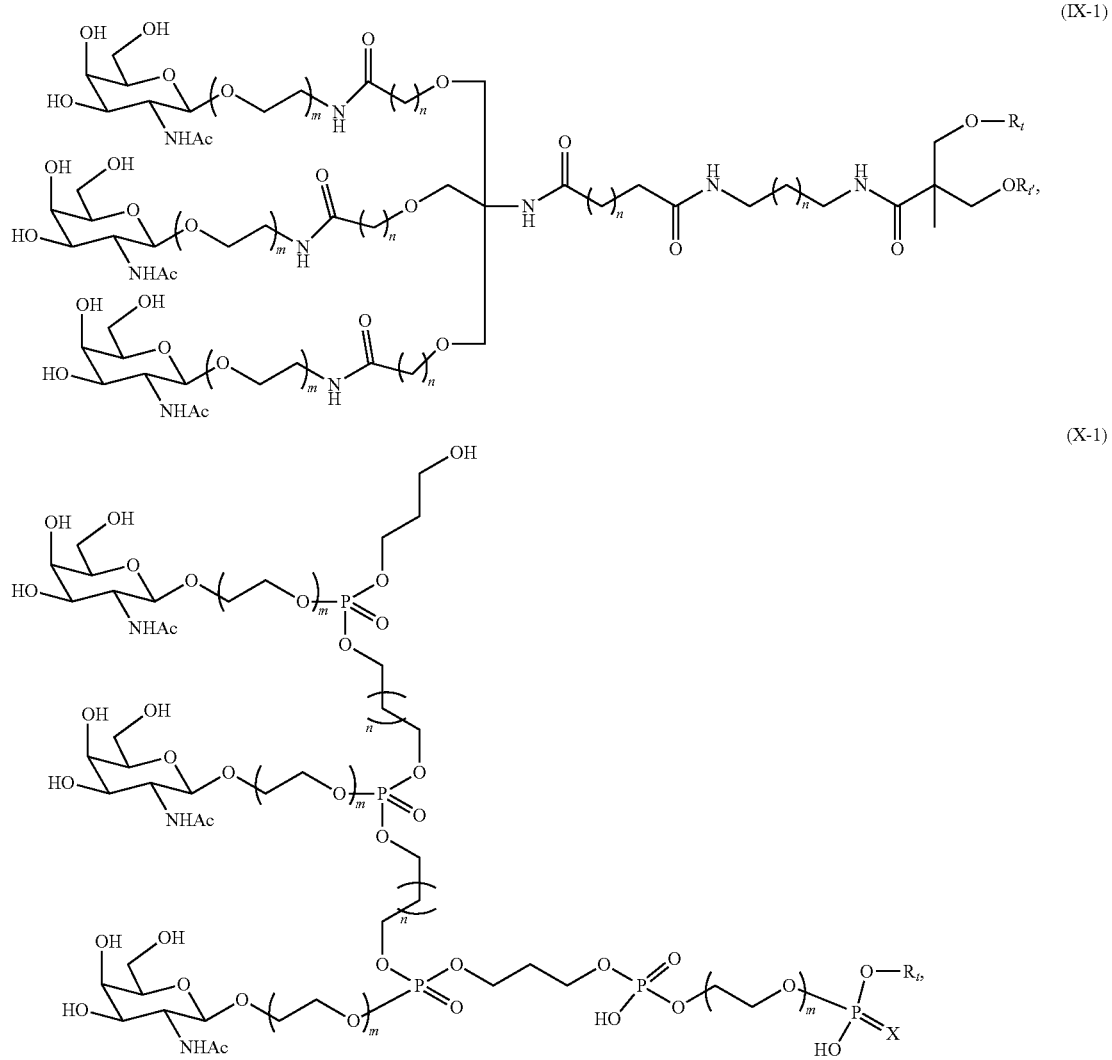

m and n on formula (IX-1) or formula (X-1) are each independently an integer of 0-6; $R_t$ and $R_{t'}$ are each independently selected from H, hydroxyl protecting group, active drug Nu, solid phase carrier, C2-C6 carboxyl, carboxylate or amide group; wherein the hydroxyl protecting group is one selected from the group consisting of 4,4'-dimethoxytrityl, 4-methoxytrityl, trityl, t-butyldimethylsilyl, 4-oxopentanoyl, 2-cyanoethyl, 4-pentenoyl and acyloxyalkyl group.

According to some embodiments of the present disclosure, the second conjugate T has a structure represented by formula (601), (602), (603), (604), (605), (606) or (607):

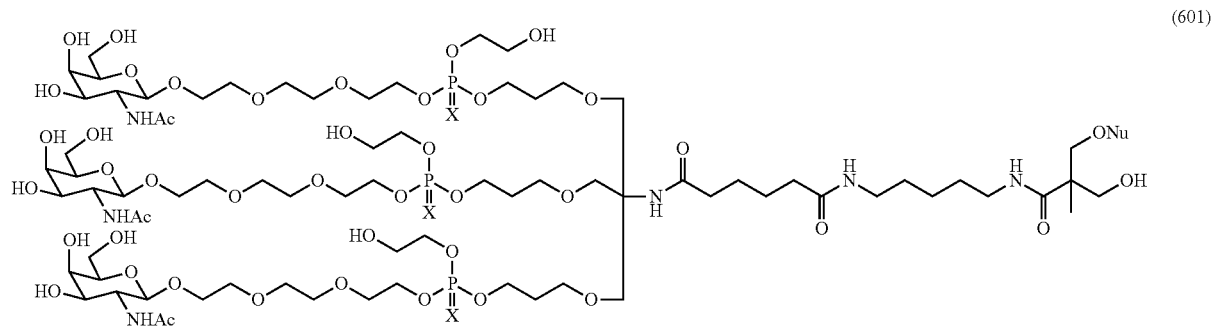

-continued
(602)
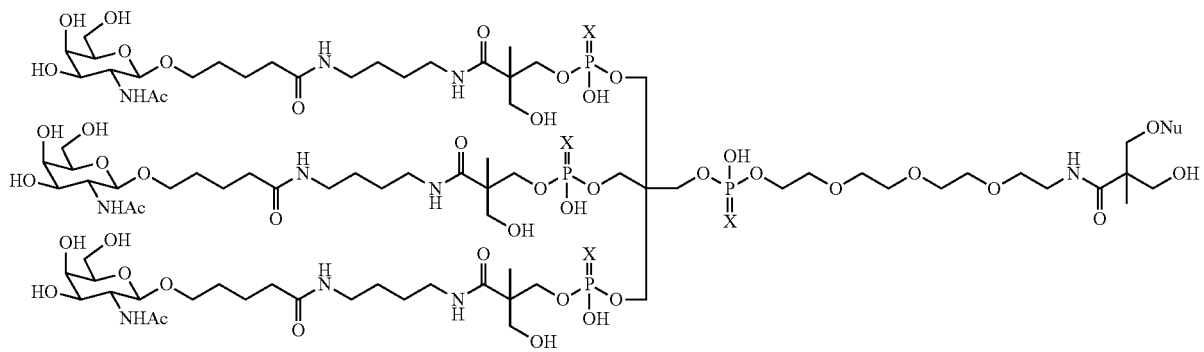
(603)
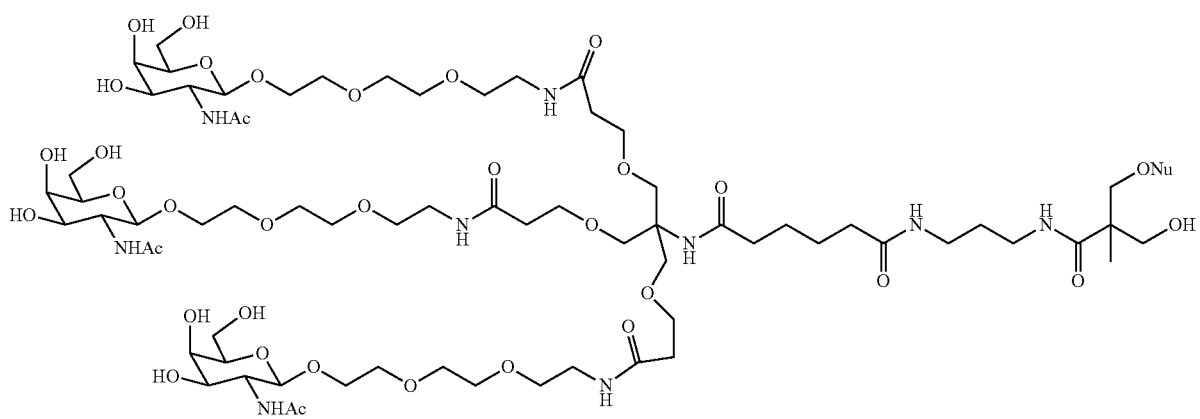
(604)
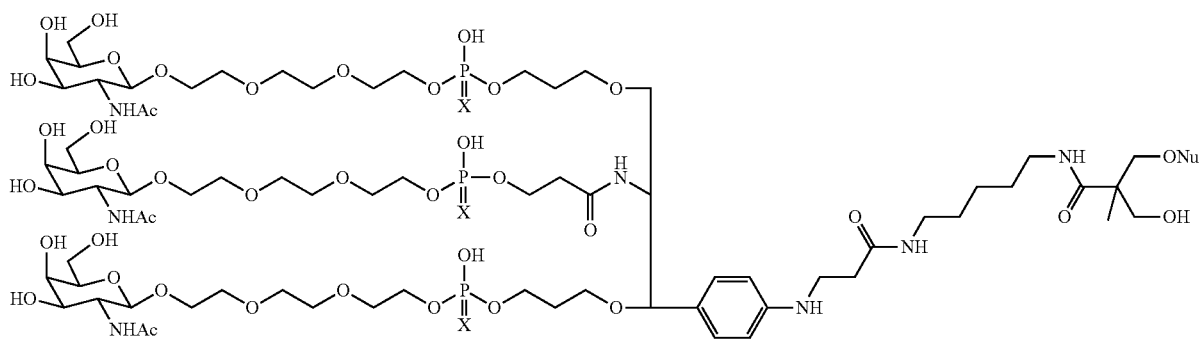
(605)
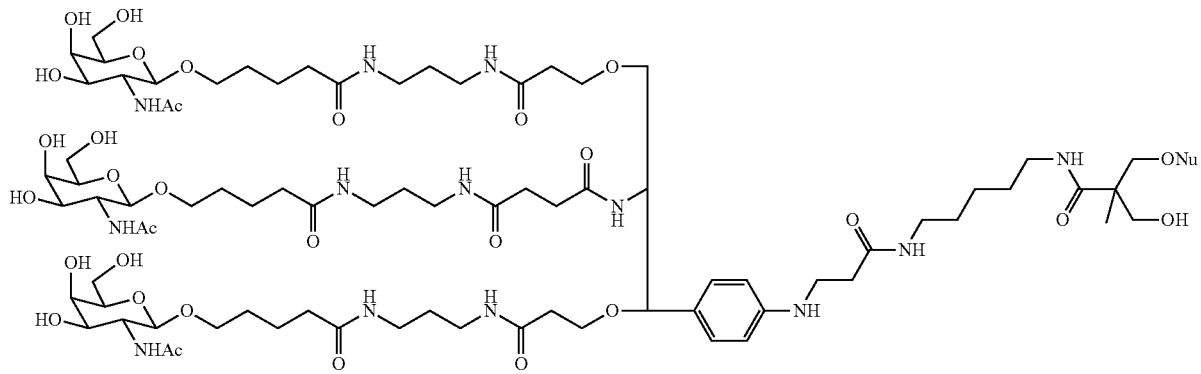

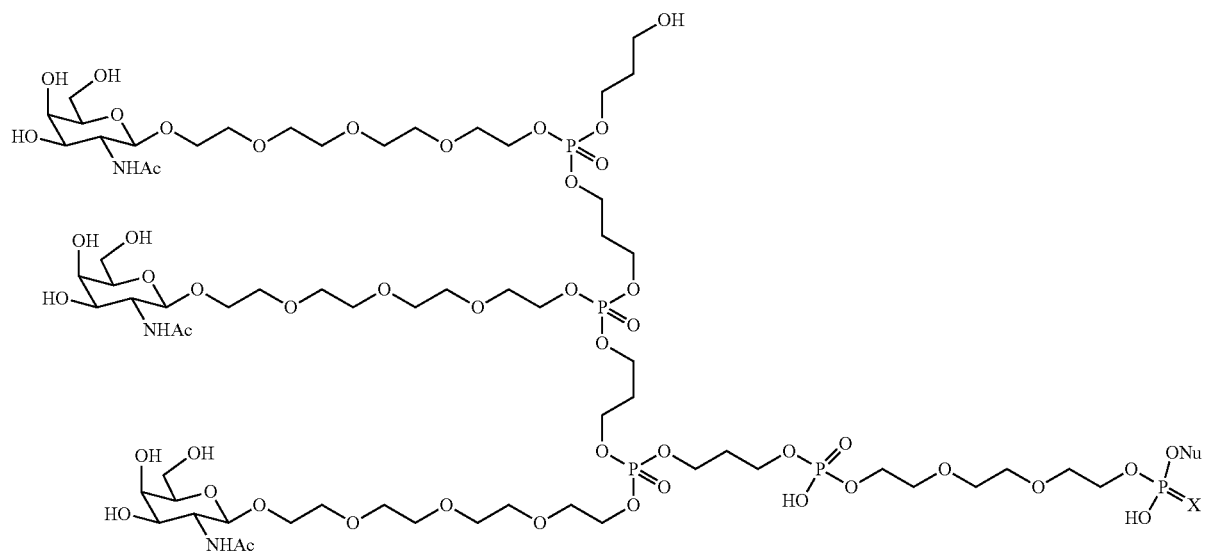

(606)

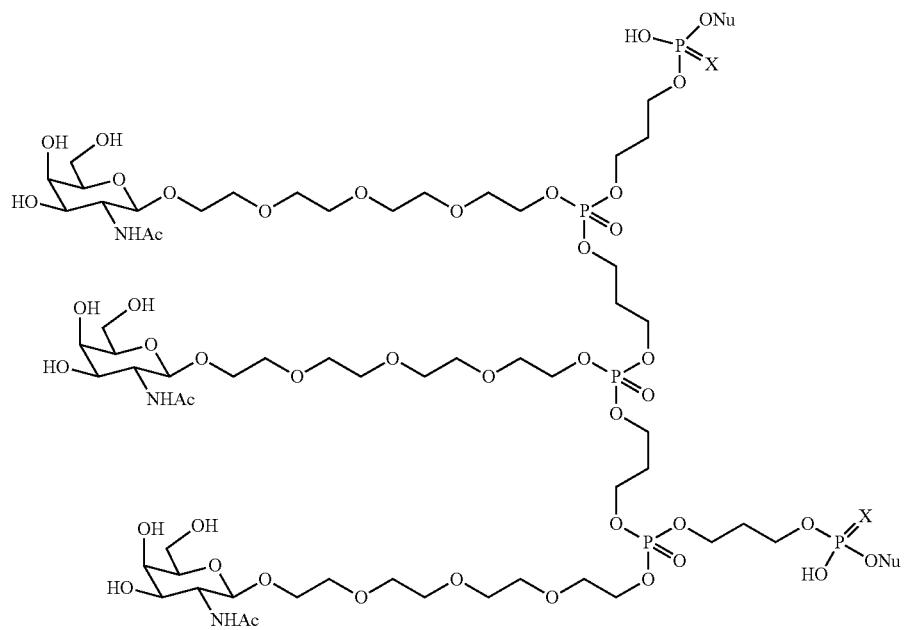

(607)

wherein X on formula (601), (602), (603), (604), (605), (606) or (607) is O or S; and Nu is an active drug small nucleic acid.

In the present disclosure, a conjugate with the structure shown by formula (603) may be obtained by contacting the compound shown by formula (603A) with an anhydride (e.g., succinic anhydride) to obtain the corresponding carboxylate (603B), the carboxylate (603B) is further connected to a solid phase to obtain a compound (603C), which is further attached on an active group Nu (e.g., a functional small nucleic acid).

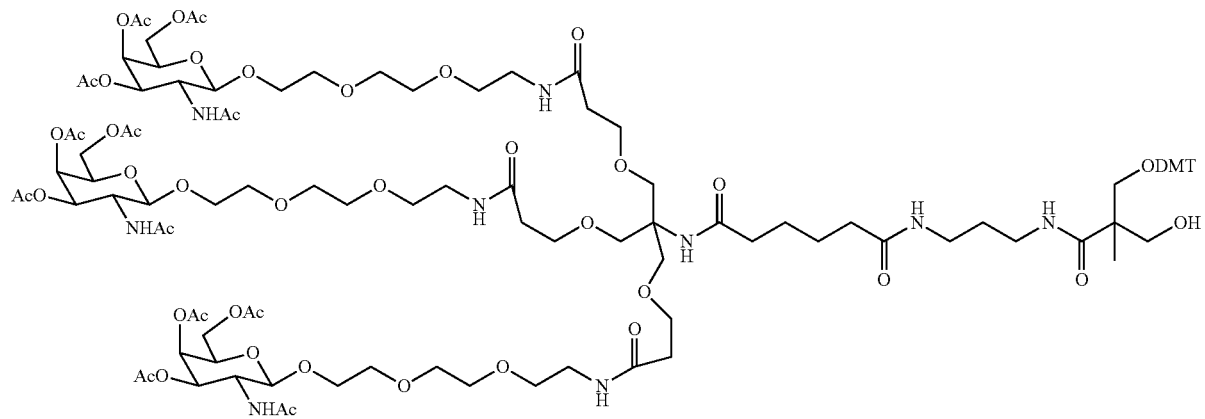

(603A)

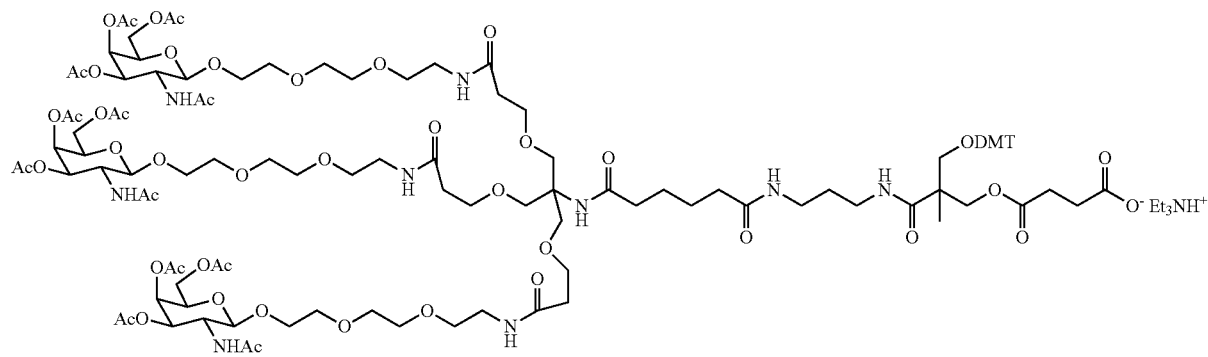

(603B)

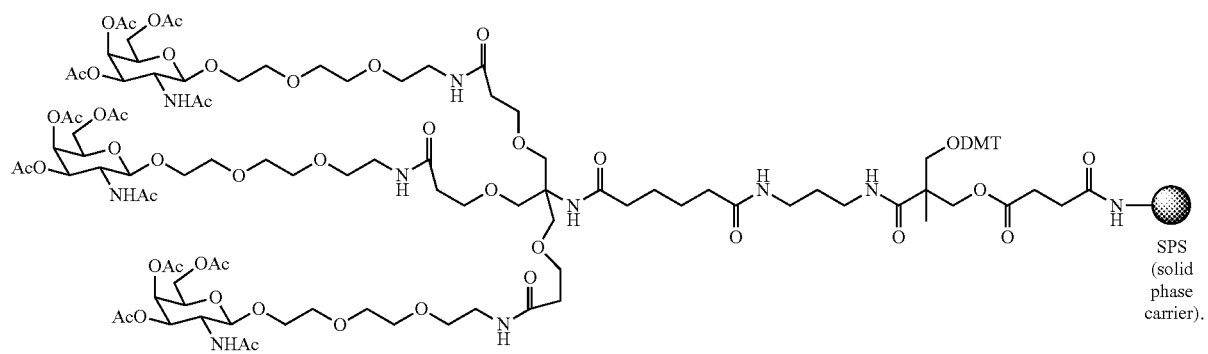

(603C)

In the present disclosure, a conjugate with the structure shown by formula (606) can be prepared from the solid phase synthesis of the compound represented by formula (101). The solid phase synthesis is not particularly limited herein, it can be a conventional choice in the art.

According to some embodiments of the present disclosure, the Nu on formula (601), (602), (603), (604), (605), (606) or (607) may be substituted by other groups having an active site.

In the present disclosure, the compound M can be prepared with the following method (the preparation of compound M shown by formula (101) is taken as an example):

(a) contacting the compound 3 with N,N,N',N'-tetraisopropyl phosphite ester and diisopropylethylamine in a first solvent under the protection of nitrogen gas to carry out a reaction; wherein the contact condition may be room temperature;

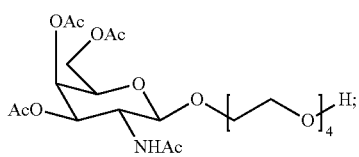

3

(b) adding 1-O-dimethoxytrityl-1,3-propanediol and ethylthiotetrazole into the above-mentioned reacted solution in the presence of a first solvent, and continuing the reaction under protection of nitrogen gas at room temperature. Wherein a molar ratio of compound 3, N,N,N',N'-tetraisopropyl phosphite ester, diisopropylethylamine, 1-O-dimethoxytrityl-1,3-propanediol and ethylthiotetrazole may be 1:(1.2-2):(2.5-3.5):(1.2-2):(0.2-0.6). The kinds and used amounts of the first solvent are not particularly limited herein, as long as the requirements of the present disclosure can be satisfied. For example, the first solvent may be dichloromethane.

compound 14, N,N-diisopropylethylamine and 2-(7-azabenzotriazo)-N,N,N',N'-tetramethylurea hexafluorophosphate may be 1:(1-1.2):(5-10):(1-1.2); preferably, a molar ratio of the part of N,N-diisopropylethylamine and the supplemented N,N-diisopropylethylamine may be 1:(0.5-1);

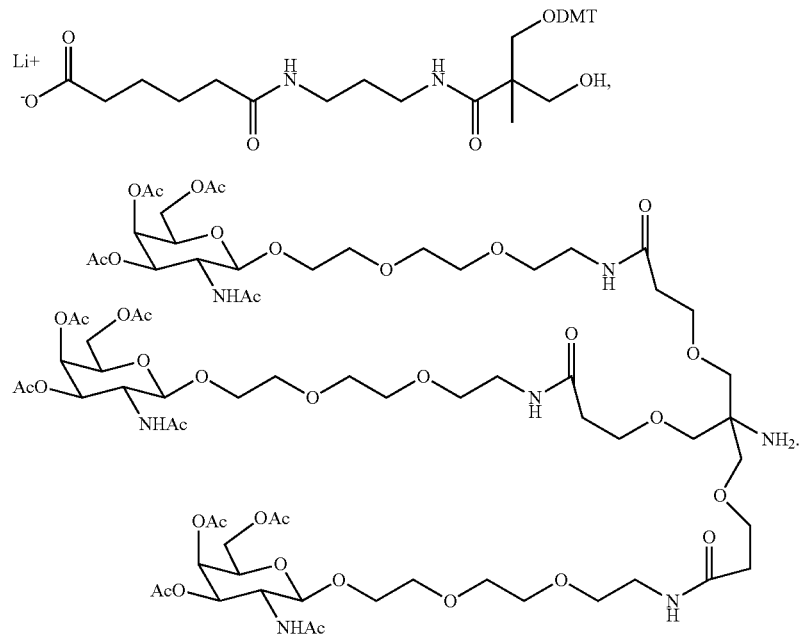

The present disclosure does not impose particular restriction on the post-treatment during preparation of the compound M, the post-treatment may be carried out in a conventional manner in the art. For example, the steps of post-treatment may comprise: washing the reacted system with saturated saline solution, and performing extraction with an extraction solvent (e.g., dichloromethane), combining concentration of the organic phase, and separating the concentrate with column chromatography to obtain compound (101).

In the present disclosure, the preparation of compound 3 can be conducted by those skilled in the art, and the present disclosure does not impose particular restriction to the preparation of compound 3, the preparation may be carried out in a conventional manner in the art.

In the present disclosure, the second conjugate T is prepared according to the following method (the preparation of compound presented by formula (603A) is taken as an example):

(a) Mixing the compound 22 with a part of N,N-diisopropylethylamine in the presence of a second solvent at room temperature to obtain a mixture, wherein a molar ratio of compound 22 to N,N-diisopropylethylamine may be 1:(3-5);

(b) Blending the aforesaid mixture with 2-(7-azabenzotriazo)-N,N,N',N'-tetramethylurea hexafluorophosphate and N,N'-diisopropylethylamine with compound 14 and stirring at the temperature condition of −5° C. to 5° C. for 0.5-1 hour; and continuing to supplement a part of N,N-diisopropylethylamine to the reaction solution at the temperature condition of −5° C. to 5° C. for 1-2 hours; wherein a molar ratio of compound 22, The kinds and used amounts of the second solvent are not particularly limited herein, as long as the requirements of the present disclosure can be satisfied. For example, the second solvent may be dichloromethane.

The present disclosure does not impose particular restriction on the post-treatment during preparation of the second conjugate T, the post-treatment may be carried out in accordance with conventional manner in the art. For example, the steps of post-treatment may comprise: gradually raising the temperature of the reacted system from 0° C. to room temperature, then continuously stirring for 2-5 hours; washing the reacted system with saturated saline solution, extracting with an extraction solvent (e.g., dichloromethane), concentrating the organic phase, and then separating by column chromatography.

In the present disclosure, preparation of compound 22 and compound 14 is well-known among those skilled in the art. The present disclosure does not impose particular restriction to the preparation of compound 22 and compound 14, the preparation may be carried out with reference to a conventional manner in the art.

According to the first conjugate and the second conjugate in the present disclosure, wherein the active functional oligonucleotide may be selected from the group consisting of the following nucleic acid substances: small interfering RNA (siRNA), microRNA, single-stranded RNA, an antisense nucleic acid, an inducing oligonucleotide, a stem loop RNA and the like; wherein the functional oligonucleotide consists of a single-stranded oligonucleotide or a double-stranded oligonucleotide. The small interfering RNA in the present disclosure is selected from a double-stranded oligonucleotide comprising a sense strand and an antisense strand, wherein the sense strand and the antisense strand are complementary, i.e., in a double-stranded nucleic acid molecule, the base of one strand and base of the other strand interact with each other by means of hydrogen bond to form the complementary pairs.

In the present disclosure, both the first conjugate and the second conjugate may be nucleic acid conjugates. Preferably, the nucleic acid conjugates are siRNA conjugates comprising the following sequences:
The Sequence of SNK-17
 Sense strand(S):
  5'-AfsmAsCfmAGfmUGfmUUfCfUfmUGfmCUfmCUfmAUfmAAf-EgGaGaGaC3 (base sequence as shown in SEQ ID NO: 1)
 Antisense Strand (AS):
  5'-mUsUfsmAUfmAGfmAGfmCAfmAmGmAAf-mCAfmCUfmGUfmUsmUsmU (base sequence as shown in SEQ ID NO: 2)
Sequence of SNK-18:
 Sense strand(S):
  5'-AfsmAsCfmAGfmUGfmUUfCfUfmUGfmCUfmCUfmAUfmAAf-TriGalNac (base sequence as shown in SEQ ID NO: 1)
 Antisense Strand (AS):
  5'-mUsUfsmAUfmAGfmAGfmCAfmAmGmAAf-mCAfmCUfmGUfmUsmUsmU (base sequence as shown in SEQ ID NO: 2).

In the present disclosure, the modified nucleotides of the above-mentioned sequences are commercially available and may be self-modified, the manner of modifying the nucleotides is well known to those skilled in the art, it may be carried out with reference to the conventional manner in the art, it is not particularly limited in the present disclosure.

In the present disclosure, an oligonucleotide conjugate can be prepared with the following method, the method comprise sequentially linking nucleoside monomers in the direction from 3' to 5' according to the kind and sequence of nucleotides of the oligonucleotide respectively under conditions of solid phase synthesis of phosphoramidites, the linking of each nucleotide monomer includes four steps of deprotection, coupling, capping, oxidation or sulfidation. In some embodiments, the method further comprises contacting a compound represented by formula (101) with the nucleoside monomer or a nucleotide sequence linked on a solid phase carrier in the presence of a coupling reagent under the coupling reaction conditions, thereby allowing the compound represented by formula (101) to be linked to the nucleotide sequence through the coupling reaction. Wherein the method further comprises a step of deprotection and cleavage with the solid phase carrier, a step of separation and purification, and optionally an annealing step.

In the present disclosure, after all the nucleoside monomers have been linked and before the annealing process, the method further comprises separating the sense and antisense strands of the siRNAs. Separation methods are well known to those skilled in the art and generally include cleaving the synthesized nucleotide sequences from a solid phase carrier to remove protecting groups on base, phosphate groups and ligands, then purifying and desalting.

In the present disclosure, the methods and specific conditions involved in the preparation of the above mentioned siRNA conjugates are well known among those skilled in the art, the method can be carried out with reference to the conventional manner in the art.

The present disclosure also provides an use of the aforementioned compound M, conjugate in the manufacture of a small nucleic acid drug;

Preferably, the specific target gene of a small nucleic acid in the small nucleic acid drug may be selected from the group consisting of PCSK9, HBV, TTR, AGT and the like.

The present disclosure will be described in detail below with reference to examples.

Unless otherwise specified in the following examples, all commercially available raw materials and reagents are used directly without subjecting to the further processing. The organic solvent is concentrated under reduced pressure by a rotary evaporator.

Compound (101) was prepared according to the following route:

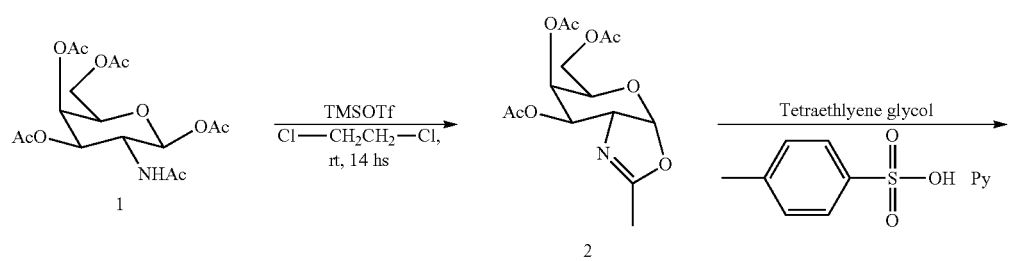

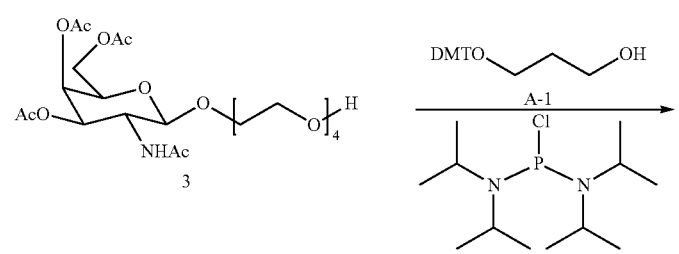

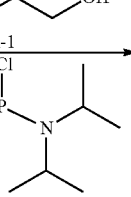

-continued

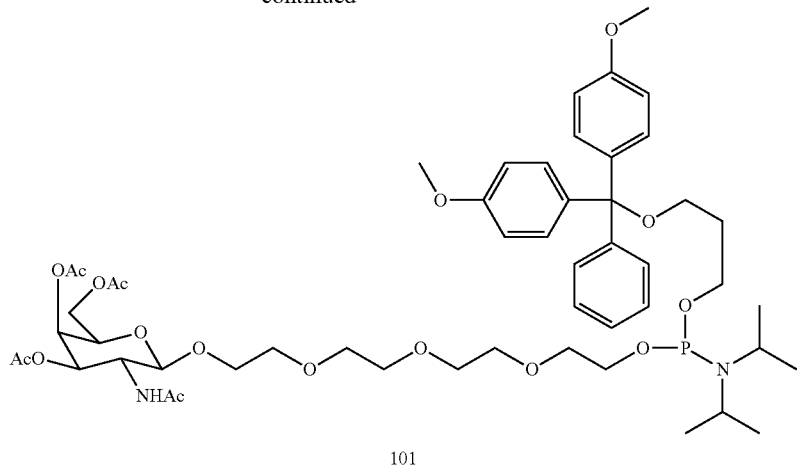

101

Synthesis of Compound 2

N-acetylgalactosamine tetraacetate 1 (10 g, 25.68 mmol) was dissolved in dichloroethane (60 mL) at room temperature, trimethylsilyl trifluoromethanesulfonate (8.6 g, 38.66 mmol) was added to the aforesaid solution under the stirring condition, stirring was continued and the solution was heated to 50° C. After reaction at 50° C. for 2 hours, the heating was stopped, and the stirring was continued for 12 hours at room temperature. The solution was poured into ice water containing saturated sodium bicarbonate, extracted with dichloromethane, and the organic phase was subjected to washing with water. The organic phase was separated out, and dried after adding anhydrous sodium sulfate, then evaporated and dried in reduced pressure to obtain a brownish-yellow foamy syrup-shaped compound 2. The compound 2 was directly used in the next step of reaction without purification.

Synthesis of compound 3

Compound 2 (5 g, 15.18 mmol) was blended with tetravinyl alcohol (29.49 g, 151.8 mmol) and pyridinium p-toluenesulfonate (3.43 g, 13.66 mmol), then heated with stirring to 80° C. and carried out reaction for 18 hours. The reaction solution was poured into a mixed solution of saturated saline solution and saturated sodium bicarbonate solution in a volumetric ratio of 1:1, and extracted with 300 mL of dichloromethane. The organic phase was separated, then dried with anhydrous sodium sulfate and evaporated under reduced pressure to a half-dry state. Purification was performed with a silica gel chromatographic column, a gradient elution was used, initially rinsed with dichloromethane, then eluted with a mixed solvent (containing ethyl acetate/methanol, 92:8, v/v), the solvent was dried under reduced pressure to obtain the near-white compound 3 (3.61 g, 45.4%). $^1$H NMR (CDCl$_3$): δ, 6.79-6.77 (1H, m), 5.31-5.29 (1H, m), 5.11-5.08 (1H, m), 4.81-4.79 (1H, m), 4.22-4.10 (7H, m), 3.93-3.89 (2H, m), 3.86-3.81 (1H, m), 3.74-3.61 (8H, m), 2.17 (3H, s), 2.17-2.15 (1H, s), 2.12 (4H, s), 2.10 (7H, m).

Synthesis of 1-O-dimethoxytrityl-1,3-propanediol (A-1)

4,4'-dimethoxytrityl chloride (18 g, 0.053 mol) was dissolved in a mixed solvent (comprising 40 mL of dichloromethane, 8.7 mL triethylamine, 0.1 mL 4-(dimethylamino) pyridine). 1,3-propanediol (21 g, 0.265 mol) was dropwise added into the abovementioned solution with stirring, and continued the stirring process at room temperature for 12 hours. The reaction solution was poured into 100 mL saturated saline solution, extracted with 300 mL of dichloromethane, the organic phase was separated, dried with anhydrous sodium sulfate, and evaporated under reduced pressure to a half-dry state. Purification was performed with a silica gel chromatographic column, a gradient elution was used, initially rinsed with a mixed solvent (containing n-hexane/ethyl acetate, 3:1, v/v), then eluted with another mixed solvent (containing n-hexane/ethyl acetate, 1:1, v/v), the solvent was dried under reduced pressure to obtain the orange compound 1-O-dimethoxytrityl-1,3-propanediol (16 g, 80%). $^1$H NMR (CDCl$_3$): δ, 7.43-7.41 (2H, m), 7.33-7.27 (6H, m), 7.29-7.27 (1H, m), 6.85-6.82 (4H, m), 3.79-3.75 (7H, m), 3.29-3.27 (2H, m), 2.20-2.18 (1H, br), 1.88-1.83 (2H, br), 1.57 (1H, s).

Synthesis of compound (101)

Compound 3 (687 mg, 1.31 mmol) was dissolved in 10 mL of dry dichloromethane, the N,N,N',N'-tetraisopropyl phosphite ester (570 mg, 2.1 mmol) and diisopropylethylamine (550 mg, 4.2 mmol) were rapidly added into the abovementioned solution. The reacted solution was stirred under protection of nitrogen gas at room temperature for 20 minutes. 1-O-dimethoxytrityl-1,3-propanediol (800 mg, 2.1 mmol) was dissolved in 5 mL of dry dichloromethane, then poured into the abovementioned solution, ethylthiotetrazole (70 mg, 0.525 mmol) was added simultaneously, the reaction was continued with stirring under protection of nitrogen gas at room temperature for 2 hours. The reacted solution was poured into saturated saline solution, extracted with 2×60 mL of dichloromethane, organic phase was separated, dried with anhydrous sodium sulfate and evaporated under reduced pressure to a semi-dry state. Purification was performed with a silica gel chromatographic column, a gradient elution was used, initially rinsed with a mixed solvent (containing N-hexane/ethyl acetate/triethylamine, 48:48:4, v/v/v), then eluted with another mixed solvent (containing ethyl acetate/triethylamine, 96:4, v/v). The solvent was dried under a reduced pressure to obtain a transparent, foamy near-white compound 101. $^1$H NMR (CD$_3$CN): δ, 7.44-7.42 (3H, m), 7.32-7.30 (6H, m), 7.29-7.21 (1H, m), 6.87-6.84

(4H, m), 6.50 (1H, m), 5.28-5.27 (1H, m), 5.00-4.97 (1H, m), 4.65-4.63 (1H, m), 4.11-4.09 (3H, m), 4.07-4.06 (3H, m), 3.97-3.95 (1H, m), 3.76 (6H, s), 3.69-3.57 (6H, m), 3.56-3.50 (8H, m), 3.11-3.10 (2H, m), 2.21 (4H, s), 1.98 (3H, s), 1.97 (3H, s), 1.94 (3H, s), 1.85 (4H, s), 1.37-1.34 (1H, m), 1.28-1.27 (1H, m), 1.20 (4H, m), 1.14 (4H, m), 1.12 (1H, m). $^{31}$P NMR (CD$_3$CN): δ, 147.95, 147.41 ppm. HRMS (ESI) m/z, C$_{52}$H$_{75}$N$_2$O$_{17}$P (M+Na$^+$+H$^+$)/2. Theoretical value: 527.56, measured value: 527.20.

Synthesis of Conjugate (603A)

1. Compound 7 was Prepared According to the Following Route:

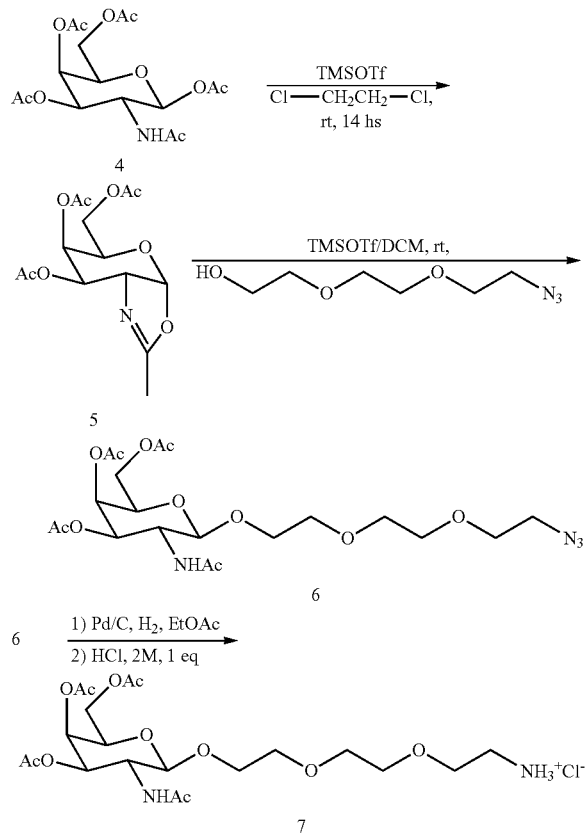

Synthesis of Compound Oxazoline 5

N-acetylgalactosamine tetraacetate 4 (10 g, 25.68 mmol) was dissolved in dichloroethane (60 mL) at room temperature, trimethylsilyl trifluoromethanesulfonate (8.6 g, 38.66 mmol) was added to the aforesaid solution under the stirring condition, stirring was continued and the solution was heated to 50° C. After reaction at 50° C. for 2 hours, the heating was stopped, and the stirring was continued for 12 hours at room temperature. The solution was poured into ice water containing saturated sodium bicarbonate, extracted with dichloromethane, and the organic phase was subjected to washing with water. The organic phase was separated out, and dried after adding anhydrous sodium sulfate, and evaporated and dried in reduced pressure to obtain a brownish-yellow foamy syrup-shaped compound 5. The compound 5 was directly used in the next step.

Synthesis of Compound 6

The compound oxazoline 5 (4.26 g, 12.9 mmol) was dissolved in dichloromethane (20 mL) at room temperature, and mixed with a solution of dry dichloromethane (20 mL) dissolved with 2-[2-(2-azidoethoxy) ethoxy] ethanol (3.4 g, 19 mmol) and stirred under the temperature condition of 0° C. Trimethylsilyl trifluoromethanesulfonate (TMSOTf, 1.4 g, 6.45 mmol) was added slowly at 0° C. into the solution and stirred for 1 hour. The mixed solution was stirred continuously for 14 hours at room temperature, the solution was then poured into ice water containing saturated sodium bicarbonate, extracted with dichloromethane (2×50 mL), and the organic phase was subjected to washing with water. The organic phase was separated out, and dried with anhydrous sodium sulfate, and rotary evaporated and concentrated in reduced pressure to a semi-dry state. Purification was further performed with a silica gel chromatographic column, a gradient elution was used, initially rinsed with a mixed solvent (containing ethyl acetate/methanol, 10:1, v/v), the product components were collected, and the solvent was drained under reduced pressure to obtain the near-white compound 6 (5.3 g, 81%). $^1$H NMR (CDCl$_3$): δ, 6.15 (d, 1H, NH), 5.32 (d, 1H, sugar-H-4'), 5.07 (dd, 1H, J=11.2 Hz, J=3.3 Hz, sugar-H-3'), 4.76 (d, 1H, J=8.6 Hz, sugar-H-1'), 4.17 (m, 3H, sugar-H-2', sugar-H-6'), 3.91 (m, 2H, —CH$_2$O), 3.89 (m, 1H, suger-H-5'), 3.76-3.61 (m, 8H, —CH$_2$O), 3.47 (m, 2H, —CH$_2$N$_3$), 2.16 (s, 3H, —CH$_3$, NHAc), 1.99, 2.00, 2.05 (3×s, 9H, —CH$_3$, Ac). HRMS (ESI) m/z, C$_{20}$H$_{32}$N$_4$O$_{11}$ (M+H$^+$). Theoretical value: 505.49, measured value: 505.20.

Synthesis of Compound 7

Azide 6 (522 mg, 1.04 mmol) was dissolved in 10 mL of ethyl acetate, Pd/C (80 mg) was added into 30 mL of ethyl acetate under the protection of nitrogen gas. The reaction bottle was connected to a hydrogen balloon, subjected to multiple replacements with hydrogen gas, the reaction bottle was connected to a hydrogen balloon at room temperature, the reaction solution was continuously stirred for 3 hours. Pd/C was filtered by the Celite, and 0.5 mL of hydrochloric acid (2M) was added dropwise and slowly, and the solution was reacted under continuous stirring for 30 minutes under a reaction temperature of 0° C. 10 mL of acetonitrile was added into the reaction solution, and subjected to azeotropic decompression concentration for twice. The concentrated solution was mixed with dichloromethane (10 mL), and concentration under reduced pressure was further performed for twice, resulting in an oily foamed crude product 7 (500 mg), which was directly used in the next step without further purification. $^1$H NMR (CDCl$_3$): δ, 8.25 (m, 2H, —NH$_2$), 5.34 (d, 1H, sugar-H-4'), 5.21 (dd, 1H, J=11.2 Hz, J=3.3 Hz, sugar-H-3'), 4.91 (d, 1H, J=8.5 Hz, sugar-H-1'), 4.12 (m, 3H, sugar-H-6', sugar-H-2'), 4.07 (m, 2H, sugar-H-5', —NH), 3.76 (m, 2H, —CH$_2$O), 3.68 (m, 2H, —CH$_2$O), 3.61 (m, 2H, —CH$_2$O), 3.58 (m, 4H, 2×—CH$_2$O), 3.20 (m, 2H, NH$_2$), 2.09 (s, 3H, —NHCO$_2$CH$_3$), 2.04, 1.96, 1.89 (3×s, 9H, —CO$_2$CH$_3$). HRMS (ESI) m/z, C$_{20}$H$_{34}$N$_2$O$_{11}$ (M+H$^+$). Theoretical values: 479.49, measured values: 479.20.

2. Compound 12 was Prepared According to the Following Route:

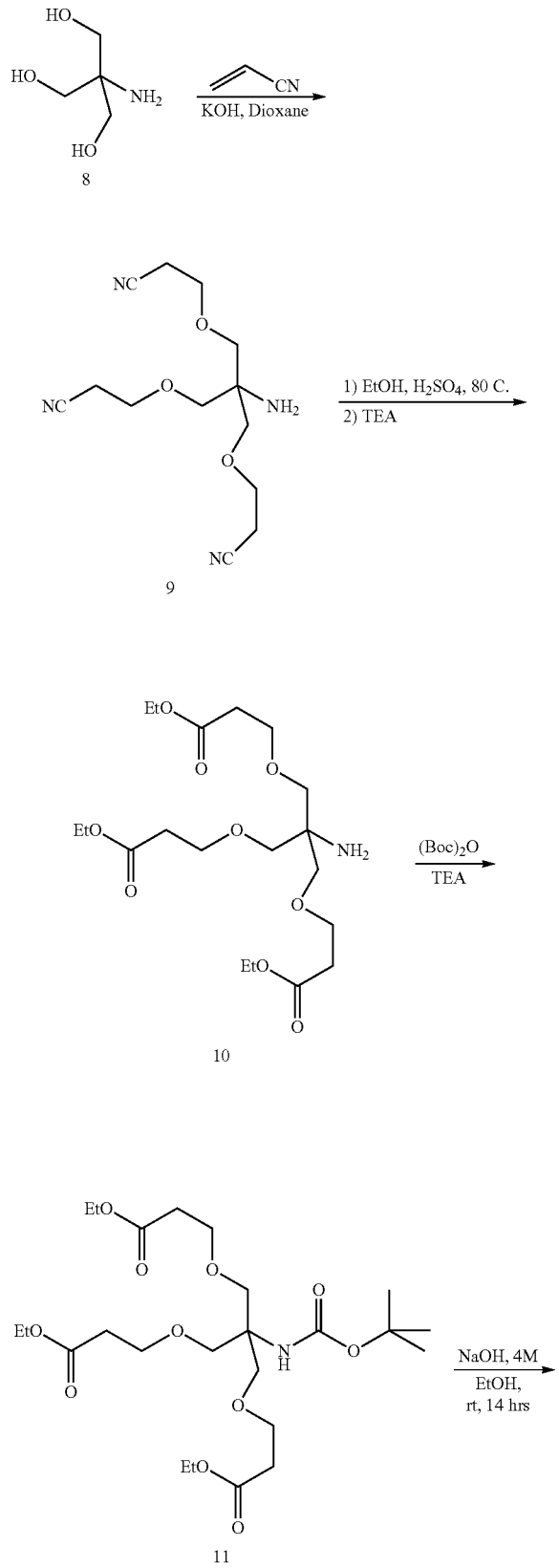

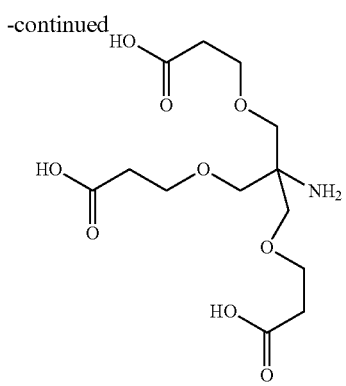

Synthesis of Compound 9

Trihydroxymethyl aminomethane 8 (10 g, 82.6 mmol) was dissolved in 15 mL of dioxane, 1.26 mL of an aqueous potassium hydroxide solution with a concentration of 40 wt % was dropwise added into the reaction solution and stirred, 20 mL of dioxane was further added at room temperature. Acrylonitrile (18 mL, 272 mmol) was added dropwise and slowly to the reaction flask under the temperature of 0° C., and the entire dropwise adding process was maintained about 1 hour. The reaction solution was continuously stirred at room temperature for 24 hours. The reaction solution was poured into a saturated sodium chloride solution, and extracted with dichloromethane (2×50 mL), the organic phase was subjected to washing with water. The organic phase was separated out and dried with the added anhydrous sodium sulfate, and rotary evaporated and concentrated in reduced pressure to a semi-dry state. Purification was further performed with a silica gel chromatographic column, the purified product was first rinsed with dichloromethane and then rinsed with a solvent mixture (containing dichloromethane/methanol, 10:1, v/v), the product components were collected. The product components were subjected to rotary evaporation and concentration in reduced pressure to obtain a pale yellow oily substance 9 (20 g, 86%). $^1$H NMR (CDCl$_3$): δ, 3.68 (t, 6H, J=7.1 Hz, 3×—CH$_2$O), 3.44 (s, 6H, 3×—CH$_2$CNH$_2$), 2.61 (t, 6H, J=6.2 Hz, 3×—CH$_2$CN), 1.70 (s, 2H, —NH$_2$). HRMS (ESI) m/z, C$_{13}$H$_{20}$N$_4$O$_3$ (M+H$^+$). Theoretical value: 281.32, measured value: 281.20.

Synthesis of Compound 10

Tri [(cyanoethoxy) methyl] aminomethane 9 (1.2 g, 4.28 mmol) was dissolved in 10 mL of anhydrous ethanol, 2 mL concentrated sulfuric acid and 10 mL anhydrous ethanol were then added dropwise and slowly to the solution in a reaction flask at room temperature. The reaction solution was heated to 80° C. and kept at reflux state for about 36 hours. After cooling the reaction solution to room temperature, 25 mL of ice solution of saturated sodium bicarbonate was added. Ethanol was distilled by rotary evaporation under reduced pressure. The aqueous solution was extracted with ethyl acetate (2×50 mL), the obtained organic phase was dried with anhydrous sodium sulfate, and then subjected to rotary evaporation and concentration in reduced pressure to obtain a pale yellow oily substance 10 (0.8 g, 46%). This crude product was directly used in the next reaction without further purification.

Synthesis of Compound 11

Crude product compound 10 (0.8 g, 1.9 mmol) was dissolved in 20 mL of dichloromethane. Di-tert-butyl dicarbonate (2 mL, 8.8 mmol) and 5 mL of triethylamine were added to the reaction solution. The reaction solution was stirred for 14 hours at room temperature. The reaction solution was poured into an aqueous solution containing saturated sodium bicarbonate, extracted with dichloromethane (2×50 mL), and the organic phase was subjected to washing with water. The organic phase was separated out, and dried with anhydrous sodium sulfate, and rotary evaporated and concentrated in reduced pressure to a semi-dry state, purification was further performed with a silica gel chromatographic column, a gradient elution was used, initially washed with dichloromethane solvent, then rinsed with a mixed solvent (containing dichloromethane/methanol, 96:4, v/v), the product components were collected, and the solvent was drained under reduced pressure to obtain a near-white oily substance 11 (0.5 g, 51%), $^1$H NMR (CDCl$_3$): δ, 4.92 (b, 1H, —CONH—), 4.14 (m, 3×2H, —CO$_2$CH$_2$—), 3.69 (m, 3×2H, —OCH$_2$—), 3.63 (s, 3×2H, —OCH$_2$—), 2.53 (m, 3×2H, —COCH$_2$—), 1.45 (s, 3×3H, —CH$_3$), 1.26 (t, 3×3H, —CH$_2$CH$_3$). HRMS (ESI) m/z, C$_{24}$H$_{43}$NO$_{11}$ (M+H$^+$). Theoretical value: 522.60, measured value: 522.40.

Synthesis of Compound 12

Boc protected compound 11 (0.6 g, 1.43 mmol) was dissolved in 20 mL of absolute ethanol, 4 mL of sodium hydroxide solution (4M) was added dropwise and slowly into the reaction solution, the temperature of reaction solution was kept at 0° C. and stirred for 14 hours. The reaction progress was monitored constantly by LC-MS, while the peak of the reactant was vanished, the reaction solution was subjected to rotary evaporation under reduced pressure, after ethanol was evaporated, 10 mL of potassium bisulfate (1M) was added to the reaction solution and continuously stirred for 15 minutes at 0° C. The reaction solution was extracted with ethyl acetate (2×50 mL), the obtained organic phase was dried with anhydrous sodium sulfate, then rotary evaporated and concentrated in reduced pressure to obtain a viscous substance 12 (0.5 g, 81%). This crude product was directly used in the next step without further purification. $^1$H NMR (CDCl$_3$): d, 9.40 (b, 3H, —CO$_2$H), 5.0 (b, 1H, —CONH—), 3.70 (m, m, 3×2H, —OCH$_2$—), 3.65 (s, 3×2H, —OCH$_2$—), 2.60 (m, 3×2H, —COCH$_2$—), 1.42 (s, 3×3H, —CH$_3$). HRMS (ESI) m/z, C$_{18}$H$_{31}$NO$_{11}$ (M+H$^+$). Theoretical values: 438.32, measured values: 438.20.

Compound 14 was Prepared According to the Following Route:

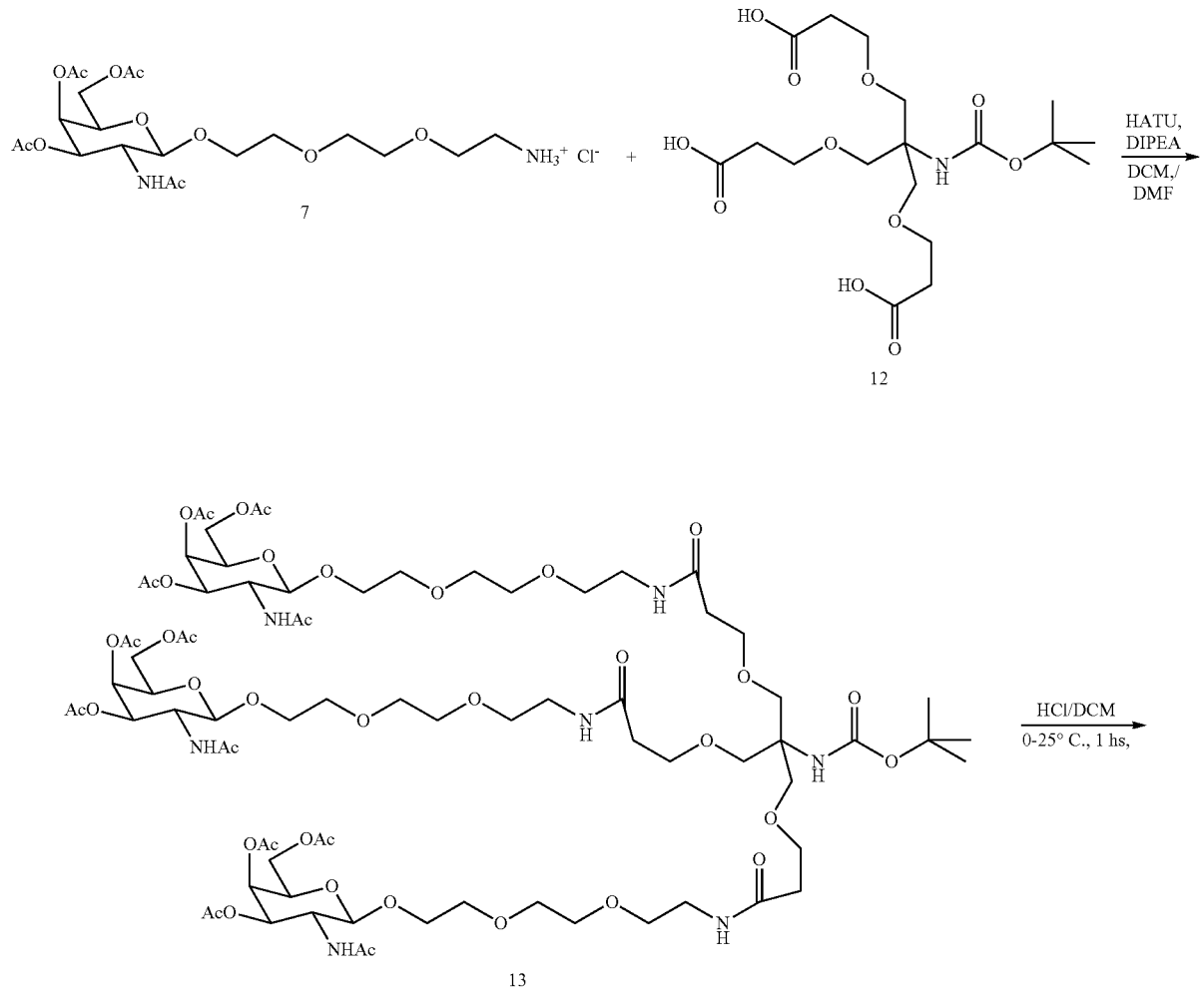

-continued

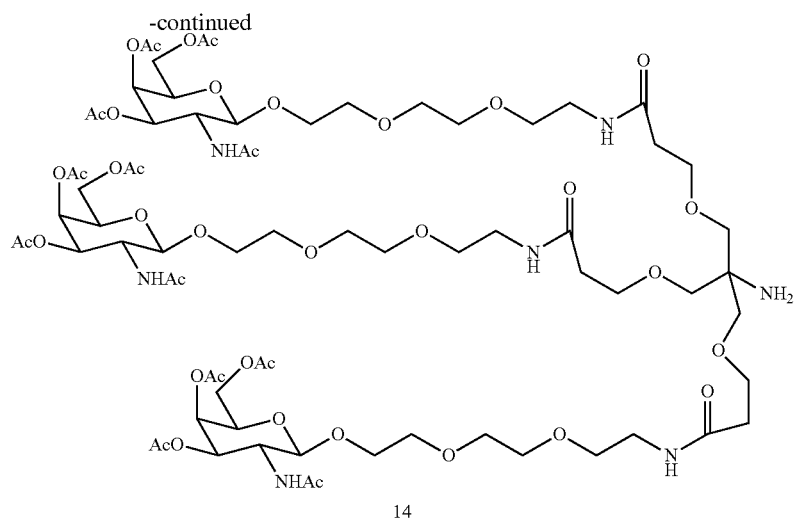

14

Synthesis of Compound 13

Tricarboxylic acid 12 (0.5 g, 1.14 mmol) was dissolved in 20 mL of dichloromethane, 2-(7-azobenzotriazole)-N,N,N', N'-tetramethylurea hexafluorophosphate (1.3 g, 3.42 mmol) and N,N-diisopropylethylamine (0.2 g, 3.95 mmol) were added, 8 mL of dimethylformamide was added simultaneously. The compound 7 (2.19 g, 4.08 mmol) was dissolved in 5 mL of dimethylformamide, and 1 mL of N,N-diisopropylethylamine was added. The two solutions were blended and stirred at room temperature and continuously stirred for 14 hours. The complete disappearance of the reactants was confirmed by the chromatographic detection. 20 mL of aqueous solution of saturated sodium bicarbonate was added into the reaction solution, and extracted with 2×50 mL of dichloromethane, the organic phase was rotary evaporated and concentrated to a semi-dry state, purification was further performed with a silica gel chromatographic column, a gradient elution was used, initially washed with dichloromethane solvent, then rinsed with a mixed solvent (containing dichloromethane/methanol, 85:15, v/v), the product components were collected, the solvent was drained under reduced pressure to obtain the near-yellow oily crude product 13 (2 g, 86%). This crude product 13 was further purified by using a reversed-phase chromatographic column, the rinsing solvent was a mixed solvent (containing $H_2O$/MeOH, 1:1, v/v), the product components were collected, then rotary evaporated and concentrated to a full dry state to obtain a compound 13 (1.24 g, 60%). $^1$H NMR (CDCl$_3$): δ, 5.32 (d, 3H, J=3.0 Hz, sugar-H-4'), 5.18 (dd, 3H, sugar-H-3'), 4.78 (d, 3H, sugar-H-1'), 4.18-4.06 (m, 24H, —OCH$_2$, sugar-H-5'), 3.93 (m, 9H, sugar-2×H-6', sugar-H-2'), 3.77, 3.64, 3.46 (m, 6H, —CH$_2$NH—), 2.44, 2.20 (m, 6H, —COCH$_2$—), 2.15 (s, 9H, —NHCOCH$_3$), 2.09 (s, 2H, —CH$_2$—), 2.05, 1.99, 1.95 (3×s, 27H, —OCOCH$_3$), 1.81 (s, 9H, CH$_3$, Boc). HRMS (ESI) m/z, C$_{78}$H$_{127}$N$_7$O$_{41}$ (M+2H$^+$)/2. Theoretical value: 910.1, measured value: 910.0.

Synthesis of Compound 14

Purified Compound 13 (2 g, 1.1 mmol) was dissolved in 30 mL of dichloromethane, 1 mL of hydrochloric acid solution (4M) and 1 mL of dioxan were slowly added into the dichloromethane reaction solution at a temperature of 0° C. The reaction solution was stirred continuously for 30 minutes at a temperature of 0° C., and then stirred continuously for 30 minutes at room temperature. The reactant was subjected to rotary evaporation and concentration to a full dry state to obtain a white foamy crude product 14 (1.7 g, 90%). This crude product was directly used in the next step without further purification. $^1$H NMR (CDCl$_3$): δ, 8.20 (b, 2H, —NH$_2$), 5.35 (d, 3H, J=3.0 Hz, sugar-H-4'), 5.22 (dd, 3H, sugar-H-3'), 4.80 (d, 3H, sugar-H-1'), 4.13 (m, 9H, sugar-2×H-6', sugar-H-2'), 3.94-3.44 (m, 24H, —OCH$_2$, sugar-H-5'), 3.77, 3.64, 3.46 (m, 6H, —CH$_2$NH—), 2.55, 2.43 (m, 6H, —COCH$_2$—), 2.15 (s, 9H, —NHCOCH$_3$), 2.09 (s, 2H, —CH$_2$—), 2.05, 1.98, 1.96 (3×s, 27H, —OCOCH$_3$). HRMS (ESI) m/z, C$_{73}$H$_{119}$N$_7$O$_{39}$ (M+H$^+$)/2. Theoretical value: 860.4, measured value: 860.0.

Compound 21 was Prepared According to the Following Route:

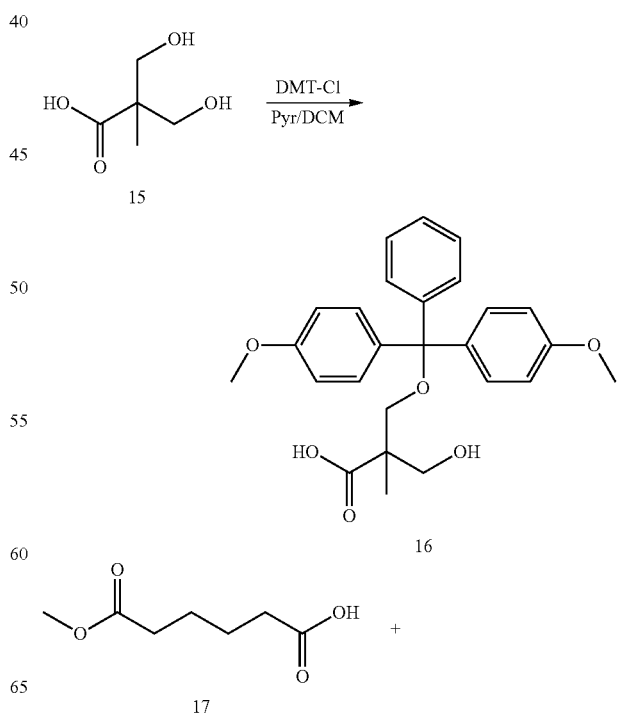

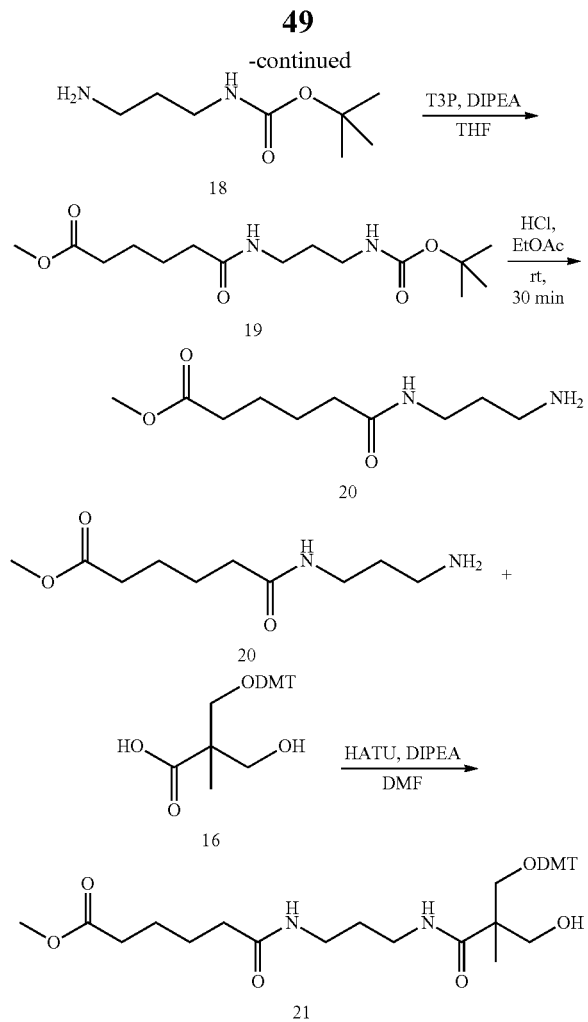

Synthesis of compound 16

4,4'-dimethoxytrityl chloride (1.8 g, 5.3 mmol) was dissolved in 5 mL of dichloromethane, the solution was added dropwise and slowly into an anhydrous pyridine (10 mL) solution containing 3-hydroxy-2-hydroxymethyl-2-methylpropanoic acid 15 (0.8 g, 5.97 mmol) at room temperature. The solution was stirred continuously for 14 hours at room temperature. 20 mL of water was added to the reaction mixture and extracted with 2×50 mL of ethyl acetate. The organic phase was subjected to rotary evaporation and concentration to a semi-dry state, purification was further performed with a silica gel chromatographic column, a gradient elution was used, initially washed with n-hexane solvent, and then eluted with a mixed solvent (containing n-hexane/ethyl acetate, 1:1, v/v), the product components were collected, the solvent was drained under reduced pressure to obtain a yellow solid 16 (1.5 g, 58%). The product 16 was directly used in the next step.

Synthesis of Compound 19

Mono-methyl adipate 17 (0.16 g, 1 mmol) and N-(tert-butoxycarbonyl)-1,3-diaminopropane N-(3-aminopropyl) tert-butyl carbamate 18 (0.174 g, 1 mmol) were dissolved in 5 mL of anhydrous tetrahydrofuran at room temperature. The solution was blended with 0.892 mL of 1-propylphosphoric acid cyclic anhydride (0.892 mL, 1.5 mmol, in 50% (volume ratio 1:1) ethyl acetate) and 0.522 mL of N,N-diisopropylethylamine (DIPEA, 0.522 mL, 3 mmol). The mixed reaction solution was continuously stirred for 30 minutes at room temperature, 20 mL of ethyl acetate was then added into the reaction solution for dilution, and 20 mL of saturated salt solution was added simultaneously, and extracted with 2×20 mL of ethyl acetate. The organic phase was separated, and dried with anhydrous sodium sulfate, then rotary evaporated and concentrated to a full dry state, resulting in a yellowish foamed crude product 19 (0.29 g, 91%), which was directly used in the next step without further purification. $^1$H NMR (CDCl$_3$), δ, 5.89 (b, 1H, —CONH—), 4.97 (b, 1H, —NHCO—), 3.75 (s, 3H, —CH$_3$), 3.27 (m, 2H), 3.15 (m, 2H), 2.34 (m, 2H), 2.19 (m, 2H), 1.67 (m 2×2H), 1.64 (m, 2H), 1.4 (s, 9H). HRMS (ESI) m/z, C$_{15}$H$_{28}$N$_2$O$_5$. Theoretical values: 316.39, measured values: 316.40.

Synthesis of Compound 20

Compound 19 (0.8 g, 2.5 mmol) was dissolved in 5 mL of ethyl acetate, the reaction solution was mixed with 3.2 mL of aqueous hydrochloric acid solution (4M), and 5 mL of dioxane was further added. The mixed reaction solution was continuously stirred for 30 minutes at room temperature. After rotary evaporation and concentration, a viscous and thick crude product 20 (0.5 g, 92%) was obtained, which was directly used for the next step.

Synthesis of Compound 21

The crude product compound 20 (0.252 g, 1 mmol) was dissolved in 5 mL of dimethylformamide, the reaction solution was blended with 3-O-4,4'-dimethoxytrityl-2-hydroxy-2-methylpropionic acid 16 (0.45 g, 0.9 mmol), and added 2-(7-azabenzotriazo)-N,N,N',N'-tetramethylurea hexafluorophosphate (0.46 g, 1.2 mmol) and N,N-diisopropylethylamine (0.52 mL) at 0° C. and stirred for 20 minutes. The reaction solution was slowly heated to room temperature and continuously stirred for 14 hours. The reaction solution was blended with 20 mL of saturated sodium chloride solution, and extracted with 2×50 mL of ethyl acetate, the organic phase was dried with anhydrous sodium sulfate and then subjected to rotary evaporation and concentration in reduced pressure to obtain a crude product 21. Purification was further performed with a silica gel chromatographic column, a gradient elution was used, initially washed with ethyl acetate solvent, followed by rinsing with a mixed solvent (containing ethyl acetate/methanol, 90:10, v/v), the product components were collected, and the solvent was drained under reduced pressure to obtain a compound 21 (0.38 g, 61%). $^1$H NMR (CDCl$_3$): δ, 8.01 (b, 1H, —CONH—), 7.26 (m, 4H, Trityl), 7.05 (m, 4H, Trityl), 6.67 (m, 4H, Trityl), 6.48 (b, 1H, —NHCO—), 5.25 (s, 3H, —OCH$_3$), 3.78 (s, 6H, 2×—OCH$_3$), 3.64 (s, 4H, 2X—CH$_2$—), 3.26 (m, 2H, —NHCH$_2$—), 3.17 (m, 2H, —CH$_2$NH—), 2.79 (m, 3H, —OCH$_3$), 2.31 (m, 2H), 2.18 (m, 2H), 1.65-1.56 (m, 6H), 1.25 (s, 3H). HRMS (ESI) m/z, C$_{36}$H$_{46}$N$_2$O$_8$, (M+Na$^+$). Theoretical value: 657.34, measured value: 657.40.

Compound (603A) was Prepared According to the Following Route:

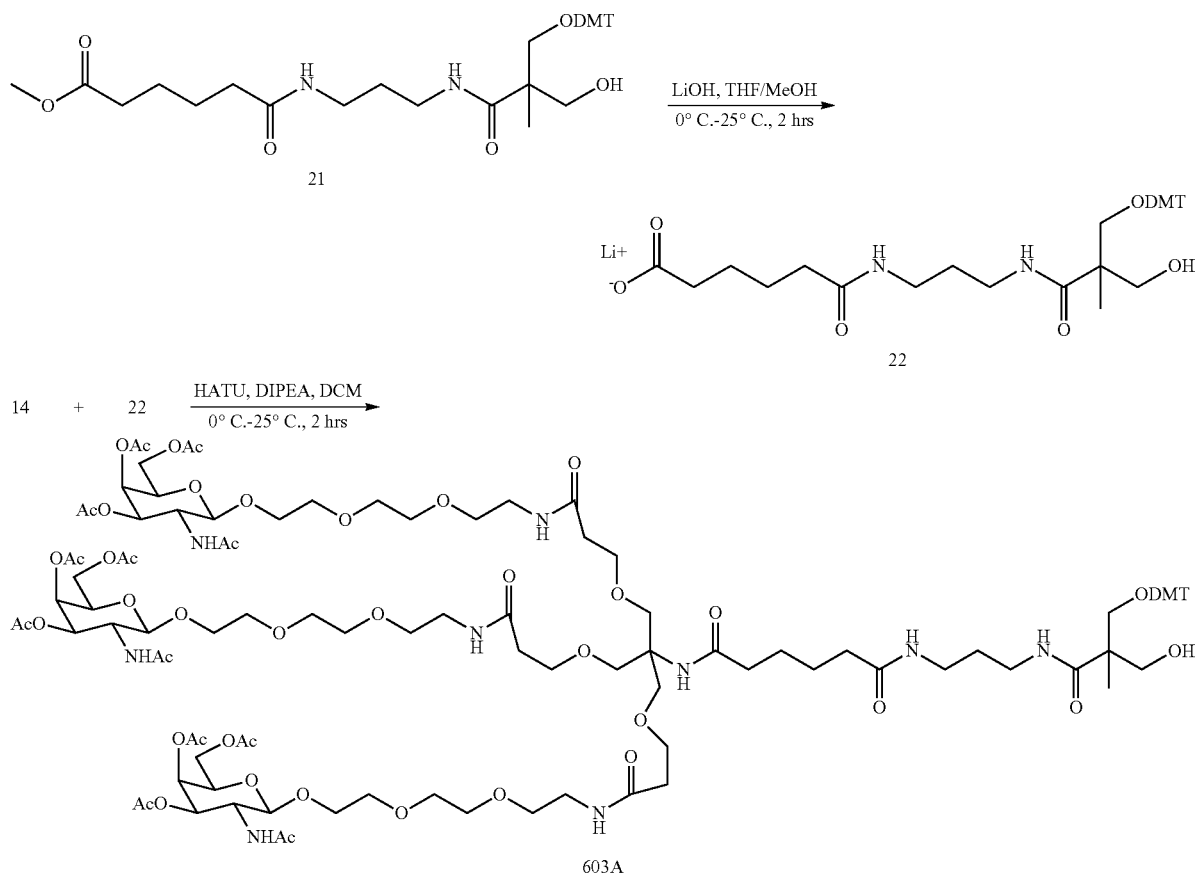

Synthesis of Compound 22

The purified compound 21 (0.7 g, 1.1 mmol) was dissolved in 5 mL of anhydrous methanol, 1.5 mL of methanol solution of lithium chloride (2M) was added slowly into the reaction solution at the temperature of 0° C. The reaction solution was stirred at 0° C. for 30 min, the reaction solution was then heated to room temperature and continuously stirred for 2 hours at room temperature. After mixing the reaction solution with 2 mL of water at room temperature, the reaction solution was subjected to rotary evaporation and concentration to a semi-dry state such that the methanol was removed, and separation was performed by using the preparative reverse phase high pressure liquid chromatography, the mobile phase solvent was methanol and water (MeOH: $H_2O$, 1:1, v/v).

The product components were collected, and the solvent was drained under reduced pressure to obtain a yellow solid compound 22 (0.66 g, 93%). $^1$H NMR (CDCl$_3$): δ, 7.38 (m, 4H, Trityl), 7.29 (b, 1H, —CONH—), 7.28 (m, 5H, Trityl), 7.16 (b, 1H, —NHCO—), 6.79 (m, 4H, Trityl), 3.76 (s, 10H, 2×—OCH$_3$, 2×—CH$_2$), 3.71 (m, 2H, —CH$_2$—), 3.21 (m, 2H, —NHCH$_2$—), 2.07 (m, 2H, —CH$_2$NH—), 1.87 (m, 2H), 1.50 (m, 2H), 1.27 (m, 2H), 1.21 (s, 3H). HRMS (ESI) m/z, $C_{35}H_{43}N_2O_8$, (M+H$^+$+Na$^+$). Theoretical value: 643.72, measured value: 643.20.

Synthesis of Compound (603A)

The purified compound 22 (0.65 g, 1.04 mmol) was dissolved in 15 mL of dichloromethane, and mixed with 0.723 mL of N,N-diisopropylethylamine (4.16 mmol) at room temperature. The mixed solution was blended with the purified compound 14 (1.83 g, 1.04 mmol), 2-(7-azabenzotriazo)-N,N,N',N'-tetramethylurea hexafluorophosphate (0.435 g, 1.1 mmol) and N,N-diisopropylethylamine (0.723 mL, 4.16 mmol) and stirred for 30 minutes under the temperature of 0° C. The reaction solution was further added with 1 mL of N,N-diisopropylethylamine and continuously stirred at 0° C. for 1 hour. The reaction temperature was gradually raised from 0° C. to room temperature, then continuously stirred for 2 hours. The reaction solution was blended with 5 mL of saturated sodium chloride solution, and extracted with 2× 50 mL of dichloromethane, the organic phase was dried with anhydrous sodium sulfate, followed by rotary evaporation and concentration in reduced pressure to obtain a crude product 603A. Purification was further performed with a silica gel chromatographic column, a gradient elution was used, initially washed with dichloromethane solvent, then rinsed with a mixed solvent (containing dichloromethane/methanol/triethylamine, 94:5:1, v/v/v), the product components were collected, and the solvent was drained under reduced pressure to obtain a yellow solid compound 603A (1.56 g, 65%). $^1$H NMR (CDCl$_3$): δ, 7.38 (m, 3H, —NH—), 7.28 (m, 4H, trityl), 7.26

(m, 1H, —NH—), 7.18 (m, 1H, —NH—), 6.84 (m, 5H, trityl), 6.37 (m, 4H, trityl), 5.33 (m, 3H, sugar-H-4'), 5.16 (dd, J=3.4 Hz, J=11.3 Hz, 3H, sugar-H-3'), 4.77 (d, J=8.4 Hz, 3H, sugar-H-1'), 4.18-4.07 (m, 3×2H, 3×1H, sugar-H-5', sugar-H-6'), 3.94 (m, 3H, sugar-H-2'), 3.77-3.53 (m, 14H), 3.42 (m, 2H, —NHCH$_2$—), 3.30-3.19 (m, 2H, —CH$_2$NH—), 2.42 (m, 2H), 2.19 (m, 4H), 2.15 (s, 9H), 2.07 (m, 2H), 2.05 (s, 9H, 2.01 (s, 9H), 1.96 (s, 9H), 1.20 (s, 3H). HRMS (ESI) m/z, C$_{87}$H$_{143}$N$_9$O$_{44}$, (M-trityl+H$^+$)/2. Theoretical value: 1,010.55, measured value: 1,010.4.

Conjugate (603B) Triethylamine Carboxylate was Prepared According to the Following Route:

and dried with anhydrous sodium sulfate, then evaporated to a semi-dry state under reduced pressure. Purification was further performed with a silica gel chromatographic column, a gradient elution was used, initially washed with a mixed solvent (containing dichloromethane/methanol/triethylamine, 100:2:1, v/v/v), further rinsed with a mixed solvent (including dichloromethane/methanol/triethylamine, 100:5:1, v/v/v), then rinsed with a mixed solvent (containing dichloromethane/methanol/triethylamine, 100:5:1, v/v/v) to obtain the final product, the solvent was drained under the reduced pressure to obtain a white compound (603B) (1.56 g, 65%). $^1$H NMR (CDCl$_3$) δ, $^1$H NMR (CDCl$_3$): δ, 7.39 (m,

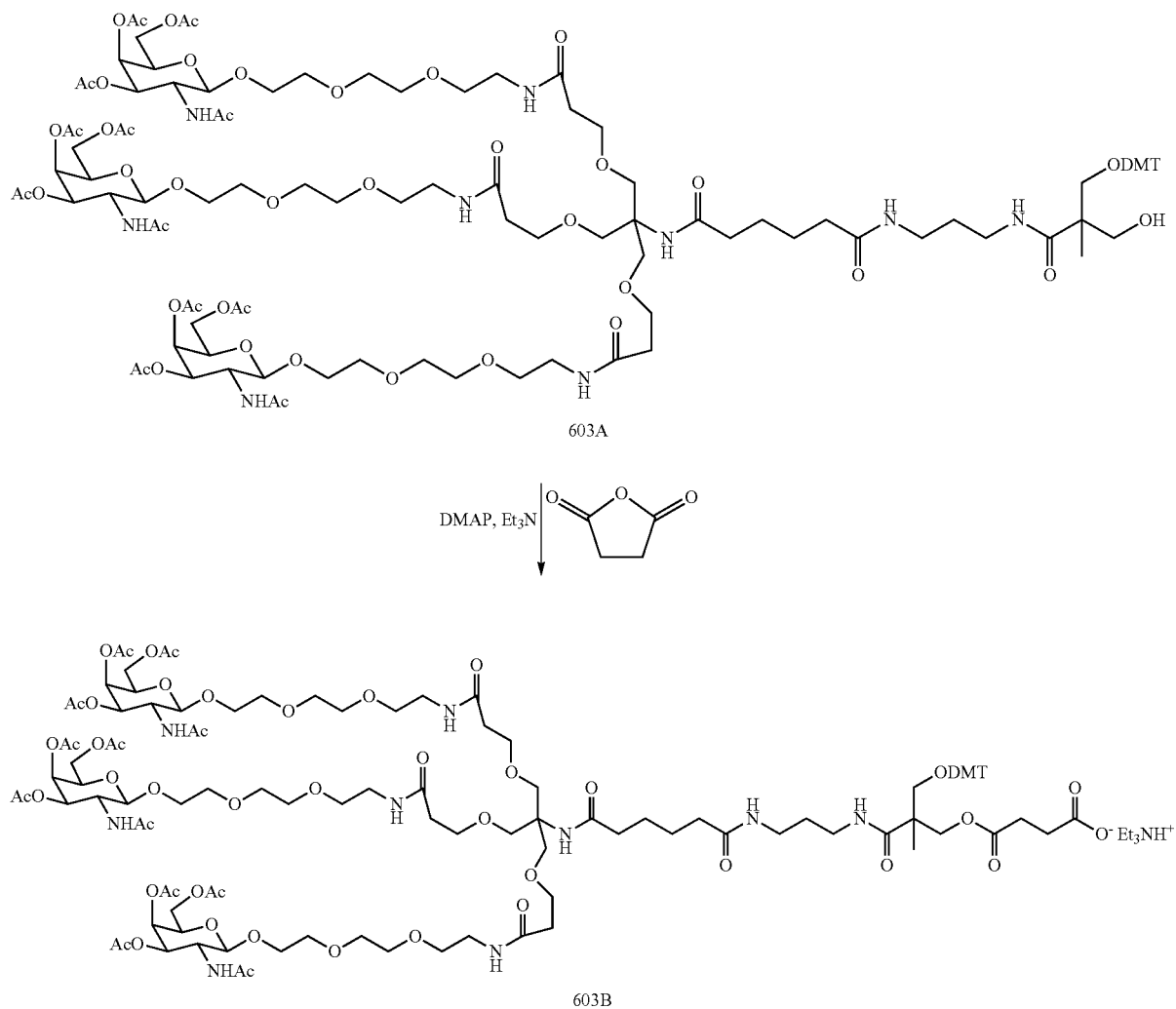

Compound (603A) (1.5 g, 0.646 mmol) was dissolved in 30 mL of dry dichloromethane, 5 mL of triethylamine was subsequently added. 4-dimethylaminopyridine (0.159 g, 1.3 mmol) was dissolved and stirred in the reaction solution, succinic anhydride (0.13 g, 1.3 mmol) was also dissolved in the reaction solution with the aid of stirring at room temperature, and the reaction was performed under stirring condition for 8 hours. Succinic anhydride (32 mg, 0.32 mmol) was further added and continuously stirred for 14 hours at room temperature. The reacted solution was then poured into a saturated saline solution, extracted with 2×50 mL of dichloromethane, the organic phase was separated, 3H, —NH—), 7.28 (m, 5H, trityl), 7.22 (m, 1H, —NH—), 7.10 (m, 1H, —NH—), 6.80 (m, 4H, trityl), 6.37 (m, 4H, trityl), 5.32 (m, 3H, sugar-H-4'), 5.29 (s, 2H), 5.15 (dd, J=3.4 Hz, J=11.3 Hz, 3H, sugar-H-3'), 4.77 (d, J=8.4 Hz, 3H, sugar-H-1'), 4.18-4.07 (m, 3×2H, 3×1H, sugar-H-5', sugar-H-6'), 3.94 (m, 3H, sugar-H-2'), 3.67 (m, 9H), 3.61-3.53 (m, 42H), 3.42 (m, 2H, —NHCH$_2$—), 3.30-3.19 (m, 2H, —CH$_2$NH—), 2.42 (m, 2H), 2.19 (m, 4H), 2.15 (s, 9H), 2.07 (m, 2H), 2.05 (s, 9H, 2.01 (s, 9H), 1.96 (s, 9H), 1.23 (s, 3H). HRMS (ESI) m/z, C$_{112}$H$_{165}$N$_9$O$_{49}$, (M–H$^+$)/2. Theoretical value: 1,209.27, measured value: 1,209.83.

Preparation of a Conjugate (603C) by Connecting the Conjugate (603B) to the Solid Phase Carrier According to the Following Process Route:

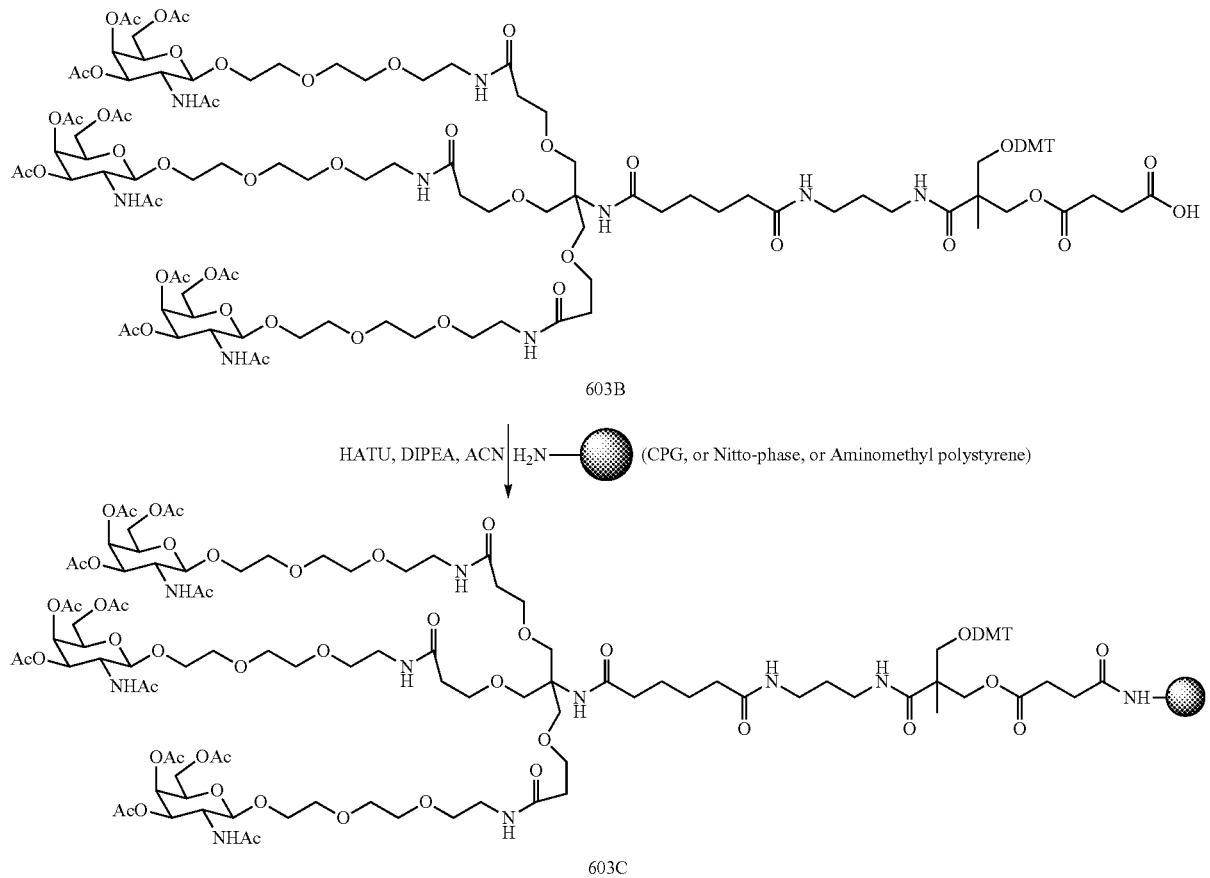

The conjugate (603B) (50 mg, 0.021 mmol) and 2-(7-azabenzotriazo)-N,N,N',N'-tetramethylurea hexafluorophosphate (10 mg, 0.026 mmol) were dissolved in 1.25 mL of anhydrous acetonitrile at room temperature. N,N-diisopropylethylamine (10 µL) was added into the reaction solution, after all reagents were dissolved, 125 mg of long-chain amino alkane glass sand (500° A, native lcaa-CPG, Chemgenes, USA) was added into the reaction solution. The solid-phase and liquid-phase were rotated and stirred for 300 rpm at room temperature. After the reaction lasted for 2 hours, the residue liquid was filtered, the long-chain amino alkane glass sand (solid phase carrier) was washed with acetonitrile for three times (3×1 mL). 0.5 mL of a tetrahydrofuran solution of capping reagent A (acetic anhydride) having a concentration of 10% (v/v) and 0.5 mL of capping reagent B (a mixed solution of N-methylimidazole, pyridine and acetonitrile at a concentration of 15:10:75, v/v/v) and the long-chain amino alkane glass sand were rotated and stirred for 1 hour at room temperature. The reaction solution was filtered, the long-chain amino alkane glass sand (solid phase carrier) was rinsed with acetonitrile for three times, then dried under reduced pressure for 2 hours by using an oil vacuum pump, a glass sand solid phase carrier (603C, 130 mg) was obtained. The solid phase carrier 603C (8.3 mg) was weighed and added into 100 mL of a dichloromethane solution of trichloroacetic acid having a concentration of 3%, then rotated and stirred for 30 seconds and stood still for 1 minute. The supernatant was taken to measure the visible light absorption at 498 nm, its light absorbance was 0.309, a loading capacity of the conjugate 603C (i.e., a loading capacity of (603B) on CPG) was calculated as 53.25 µmol/g.

Preparation of Sense and Antisense Sequences of TTR siRNA (Preparation of siRNA Conjugate).

The small interfering RNA of the present disclosure was selected from double-stranded oligonucleotides comprising a sense strand and an antisense strand, wherein the sense and antisense strands were complementary, i.e., base of one strand and base of the other strand in a double-stranded nucleic acid molecule formed complementary pairs by hydrogen-bond interaction. In double-stranded helical oligonucleotides, the purine base adenine (A) was paired with the pyrimidine base thymine (T) or uracil (U); the purine base guanine (G) was consistently paired with the pyrimidine base cytosine (C). The two complementary strands had a sequence ranging from 5'- to 3'- and a sequence ranging from 3'- to 5'-respectively. Each nucleotide in the small interfering RNA was independently a modified or unmodified nucleotide, wherein the modification denoted that the 2'-hydroxyl group was substituted by another group. The modification at the 2'-site of the nucleotide may be selected from 2'-methoxy, 2'-fluoro, 2'-methoxyethyl, 2'-2,4-dinitrophenol, 2'-amine group, 2'-4'-loop-locked ethyl group and other group. Each nucleoside of the sequence was linked via a phosphodiester bond, wherein a single oxygen atom of the phosphodiester bond was substituted by a sulfur atom to form a phosphorothioate diester bond. The sequence of a sense strand and an antisense strand was typically composed of 19 (or 21) nucleotides in length, and formed a double stranded pairing in a complementary manner. The sequence of the sense strand nucleotide was a section of nucleotide in the target mRNA. The antisense strand was typically linked with 2 contiguous deoxythymine nucleotides or 2 contiguous uracil nucleotides. The target mRNA was typically mRNA of a gene aberrantly expressing proteins in cells.

The functional oligonucleotide conjugate may be prepared according to the technological process shown in FIG. 1.

Pursuant to the solid phase synthesis method of phosphoramidites, the nucleoside monomers were linked one by one according to the sequence along the direction from 3'-5' according to the above sequence. Each linking with a single nucleoside monomer included the four-step reaction of deprotection, coupling, capping and oxidation.

Formulation of Solid Phase Synthesis Reagent:

The deprotection reagent was a dichloromethane solution of trichloroacetic acid (TCA) or dichloroacetic acid (DCA) having a concentration of 3% (v/v). The nucleoside monomers were dissolved in anhydrous acetonitrile having a concentration of 0.05-0.1M, which was added with a small amount of molecular sieve 3A° for anhydrous treatment. The coupling activator was anhydrous acetonitrile of 5-ethylthio-1H-tetrazole having a concentration of 0.25M or 0.45M, alternatively the activator may be selected from 1H-hetrazole, 5-benzyylthio-1H-tetrazole and 4,5-dicyanoimidazole. The capping reagent A was a tetrahydrofuran solution of acetic anhydride having a concentration of 10% (v/v). The capping reagent B was a mixed solvent of N-methylimidazole, pyridine and acetonitrile having a concentration of 15:10:75 (v/v/v). The oxidizing reagent was the water and pyridine solution of iodine having a concentration of 0.05M (95 wt % of an aqueous pyridine solution). The sulfurization reagent was N-dimethylaminomethylidene) amino]-3H-1,2, 4-dithiazoline-3-thione having a concentration of 0.05M (pyridine/acetonitrile, 2:3, v/v). The deprotection reagent was concentrated aqueous ammonia with a concentration of 28 wt. %.

Wherein the solid phase carrier for solid phase synthesis of nucleotides was commercially available and commonly used solid phase carrier (NittoPhase® HL UnyLinker™ 300; or 500° A, native lcaa-CPG, Chemgenes, USA).

Steps of Solid Phase Synthesis:

A solid phase carrier was blended with a dichloromethane solution of trichloroacetic acid having a concentration of 3% (v/v) with a molar ratio of 1:30 on a synthesizer. The reaction was performed for 1.5 minutes at room temperature, and the operation was repeated for three times, the dropwise adding of a deprotection reagent was stopped when the color of elution solution of solid phase carrier was changed from red color to colorless. After repeated washing with anhydrous acetonitrile, the nucleoside monomer and activator (coupling activator, 5-ethylthio tetrazole) were added (at a molar ratio of nucleoside monomer to activator of 1:20), and a molar ratio of the solid phase carrier and nucleoside monomer were 1:(5-6). The reagents were at room temperature and the time of the solid phase reaction was 3-4 minutes for one cycle, and after two cycles, the reaction was stopped. After washing with anhydrous acctonitrile, the oxidizing reagent solution was added, a molar ratio of the solid phase carrier and the oxidizing reagent were 1:6. The reaction time of the oxidizing reagent and the solid phase carrier at room temperature was about 2 minutes, the operation was repeated twice. After the coupling reaction, if a sulfidation reaction step was required, the sulfidation reagent solution was added, a molar ratio of the solid phase carrier and the sulfidation reagent was 1:6. The reaction time of the sulfidation reagent and the solid phase carrier at room temperature was about 4-5 minutes, and the operation was repeated twice. The capping protection reaction was performed by adding the capping reagent, a molar ratio of the solid phase carrier and the capping reagent was 1:80. The reaction time of the capping reagent and the solid phase carrier at room temperature was about 1-2 minutes, and the operation was repeated twice. The aforementioned deprotection, coupling, oxidizing and capping steps were cycled until the coupling of the last nucleotide was completed. The solid phase carrier loaded with the sense strand or the antisense strand of the nucleic acid sequence was transferred into a vial bottle, an aqueous ammonia solution having a concentration of 28% was added, and the glass cap was screwed tightly for sealing, the base protecting group of the sense strand or the antisense strand was hydrolyzed and removed at the temperature of 55° C., while the sense strand or the antisense strand was hydrolyzed and separated from the solid phase carrier. The reaction was run for 16 hours. The resulting solution of the small nucleic acid strand was filtered and separated from the solid phase carrier. After concentration, a crude product of the small nucleic acid strand was obtained.

Purification, Separation and Desalting by Using the Preparative High Pressure Liquid Chromatography Small nucleic acid was purified by gradient elution of NaBr using a preparative type anion exchange chromatographic column (Source 15Q). Mobile phase A: 20 mM sodium phosphate (pH 8.0), mobile phase B: 20 mM sodium phosphate (pH 8.0), 1M sodium bromide in aqueous acetonitrile having a concentration of 10%. The column temperature was 65° C. The flow rate was 10 mL/min. The elution gradient was initiated a mobile phase A, followed by a change in mobile phase B from 0% to 20% at 12 minutes. The mobile phase B increased from 20% to 50% in the subsequent 15 minutes. The eluent was collected, and subjected to component analysis and component combination. Desalting was performed by using a reverse phase chromatography purification column, or a dialysis desalting process. The eluent was subjected to concentration and freeze drying to obtain purified small nucleotides. For the synthesized sense and antisense strands, purity was detected using the anion exchange liquid chromatogram (AEX-HPLC), and the full sequence molecular weight was identified and analyzed by reverse phase liquid chromatography-mass spectrometry (LC-MS), the measured value for molecular weight was consistent with the theoretical value to confirm success in synthesizing the nucleic acid sequence.

Annealing

The synthesized sense strand (S strand) and antisense strand (AS strand) were blended at an equimolar ratio in a normal saline for injection, heated at a temperature of 90° C. for 5 minutes, then cooled slowly to room temperature and stored in a refrigerator at 4° C. for 12 hours to form double-stranded structure via hydrogen bond, the siRNA conjugate (comprising the SNK-17 sequence and SNK-18 sequence) was obtained.

Targeted Mice TTR siRNA was a Sequence Numbered SNK-17:

Sense strand(S):

5'-AfsmAsCfmAGfmUGfmUUfCfUfmUGfmCUfmCUfmAUfmAAf-EgGaGaGaC3 (base sequence as shown in SEQ ID NO: 1)

Antisense Strand (AS):

5'-mUsUfsmAUfmAGfmAGfmCAfmAmGmAAf-mCAfmCUfmGUfmUsmUsmU (base sequence as shown in SEQ ID NO: 2)

Targeted Mice TTR siRNA was a Sequence Numbered SNK-18:

Sense strand(S):

5'-AfsmAsCfmAGfmUGfmUUfCfUfmUGfmCUfmCUf-mAUfmAAf-TriGalNac (base sequence as shown in SEQ ID NO: 1)

Antisense Strand (AS):

5'-mUsUfsmAUfmAGfmAGfmCAfmAmGmAAf-mCAfmCUfmGUfmUsmUsmU (base sequence as shown in SEQ ID NO: 2)

S: sense strand; AS: antisense strand wherein the uppercase C, G, U, A represent base of nucleotides; the lowercase m indicates that the nucleotide adjacent to the right side of the letter m is a 2'-methoxy modified nucleotide (i.e., the 2'-OH of the pentose in the nucleotide is substituted by methoxy); the lowercase letter f indicates that the nucleotide adjacent to the left side of the letter f is a 2'-fluoro modified nucleotide (i.e., the 2'-OH of the pentose in the nucleotide is substituted by fluorine); the lowercase letter s indicates that two nucleotides adjacent to the left side and right side of the letter s are connected via a thiophosphate diester bond (i.e., the non-bridging oxygen atom in the phosphodiester bond is substituted by sulfur atom); no other letter between two nucleotides adjacent to the left and right sides indicates a linking with a phosphodiester bond. TriGalNac denotes a moiety of formula (603) other than Nu, Eg denotes ethylene glycol, three Ga indicates the compound (606) prepared with a single N-acetylgalactosamine (represented by formula (101)) (by means of a solid phase synthesis process), and C3 is 1,3-propanediol.

The LC/MS analysis data confirmed that the sense strand (S) of SNK-17, HRMS (ESI) m/z theoretical value: 8,704.23; measured value: 8,704.0; the antisense strand (A) of SNK-17, HRMS (ESI) m/z theoretical value: 7,595.43, measured value: 7595.0. The sense strand(S) of SNK-18, HRMS (ESI) m/z theoretical value: 8,503.94; measured value: 8,503.1; the antisense strand (A) of SNK-18, HRMS (ESI) m/z theoretical value: 7,595.43, the measured value: 7,595.0.

Activity Test (Biological Activity Test for Targeting Mice TTR)

The female C57BL/6 mice (4-6 weeks old) were randomly grouped based on the body weight, 5 mg/kg of the prepared siRNA conjugate (SNK-17) was injected into the mice on the zero day, the mice were killed on the 21$^{st}$ day and the liver tissues were taken, the RNA was extracted according to the instructions of the RNAeasy Mini kit (QIAGEN, Article No. 74104). Control group was performed by injecting normal saline without drug. RT-PCR was performed according to the recommendation of High Capacity cDNA Reverse Transcription Kits (Thermo Fisher, Article No. 4368814), 1 μg of RNA was contained in each reaction. The gene expression was quantified by using the real-time fluorescence PCR method, and the TaqMan probe of mice TTR was Mm00443267_ml, and the probe of the internal reference gene (mice HPRT) was Mm03024075_ml (Thermo Fisher Scientific, Waltham, MA, USA). The PCR conditions were 1 cycle for 20 sec at the temperature of 95° C., 40 cycles of 1 sec at 95° C. and 20 sec at 60° C., and the real-time fluorescence PCR instrument was StepOne Plus (Thermo Fisher). The TTR gene expression was calculated based on the 2^-ΔΔCt, and the mice HPRT gene expression was used as the internal reference. The expression level of TTR gene in liver was expressed as a percentage of treated group vs. control group (see FIG. 2).

The female C57BL/6 mice (4-6 weeks old) were randomly grouped based on the body weight, 5 mg/kg of the siRNA (SNK-18) was injected into the mice on the zero day, the 2$^{nd}$ day and the 4$^{th}$ day, the mice were killed on the 21$^{st}$ day and the liver tissues were taken, the RNA was extracted according to the instructions of the RNAeasy Mini kit (QIAGEN, Article No. 74104). Control group was performed by injecting normal saline without drug. RT-PCR was performed according to the recommendation of High Capacity cDNA Reverse Transcription Kits (Thermo Fisher, Article No. 4368814), 1 μg of RNA was contained in each reaction. The gene expression was quantified by using the real-time fluorescence PCR method, and the TaqMan probe of mice TTR was Mm00443267_ml, and the probe of the internal reference gene (mice HPRT) was Mm03024075_ml (Thermo Fisher Scientific, Waltham, MA, USA). The PCR conditions were 1 cycle for 20 sec at the temperature of 95° C., 40 cycles of 1 sec at 95° C. and 20 sec at 60° C., and the real-time fluorescence PCR instrument was StepOne Plus (Thermo Fisher). The TTR gene expression was calculated based on the 2^-ΔΔCt, and the mice HPRT gene expression was used as the internal reference. The expression level of TTR gene in liver was expressed as a percentage of treated group vs. control group (see FIG. 3).

Figure 2:
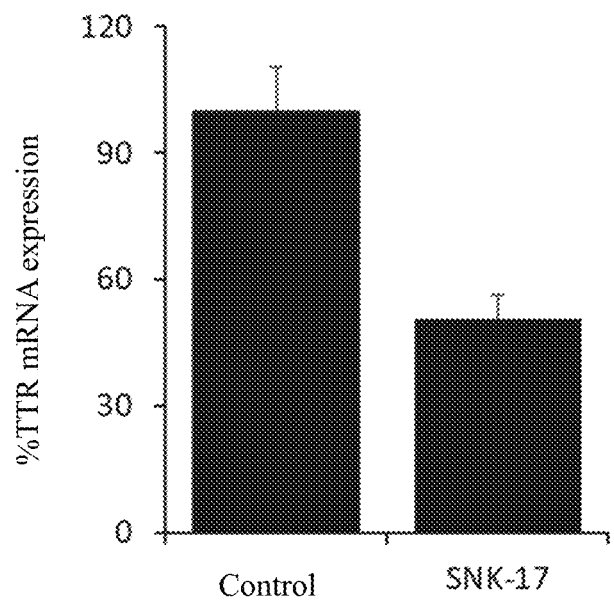
FIG. 2 shows the result of siRNA (SNK-17) for reducing TTR mRNA expression level in liver of C57BL/6 mice.
Figure 3:
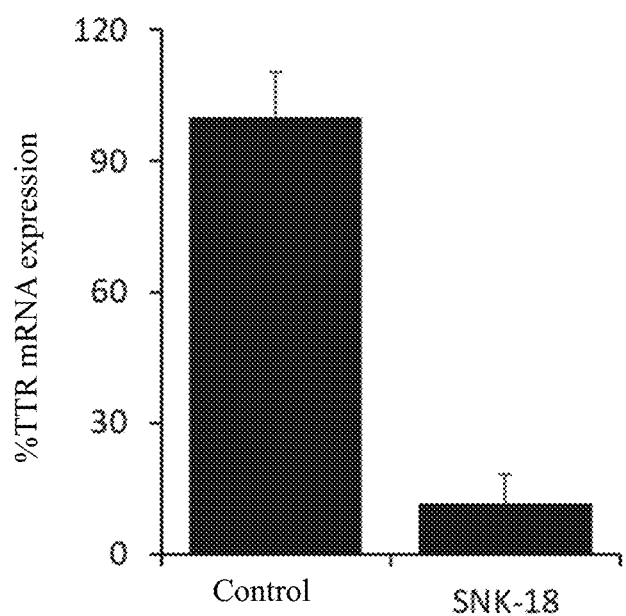
FIG. 3 shows the result of siRNA (SNK-18) for reducing TTR mRNA expression level in liver of C57BL/6 mice.

As can be seen from FIG. 2 and FIG. 3, the conjugates of the present disclosure are capable of delivering small nucleic acid in a directional manner, the in vivo stability is strong. Further experiments have demonstrated that the double stranded oligonucleotides or oligonucleotide conjugates provided by the present disclosure have higher stability, lower toxicity and/or improved inhibitory activity of liver TTR mRNA expression.

The superior effect of inhibiting replication of hepatitis B virus can be obtained by using siRNA-100 comprising a sense strand with base sequence 5'-CUAGGAGGCU-GUAGGCAUAAA-3' (SEQ ID NO:3) and an antisense strand with base sequence 5'-UUUAUGCCUACAGCCUC-CUAG-3' (SEQ ID NO: 4) as an active drug. Further, the siRNA-100 is modified in such a manner that the modified siRNA has a more stable nucleic acid structure, and the base pairing with a higher specificity and affinity; in addition, the siRNA having the following modifications exhibits a more excellent in vivo inhibitory effect, which can further reduce the in vivo immunogenicity of the siRNA in the present disclosure (for details, refer to the description of a title of invention "A NUCLEIC ACID TARGETING HEPATITIS B VIRUS AND USES THEREOF", CN114621951A published by the present inventors):

5'-CsUsAGGAGfGCfUGfUAGGCAUAAA-3' (SEQ ID NO: 5)

5'-UsUfsUAfUGfCCUACAGCfCUCCUAGsUSU-3' (SEQ ID NO: 6)

wherein the lowercase letter f indicates that the nucleotide adjacent to the left side of the letter f is a 2'-fluoro modified nucleotide (i.e., the 2'-OH of the pentose in the nucleotide is substituted by fluorine); the lowercase letter s indicates that two nucleotides adjacent to the left side and right side of the letter s are connected via a thiophosphate diester bond (i.e., the non-bridging oxygen atom in the phosphodiester bond is substituted by sulfur atom); the underlined nucleotide indicates that the 2' hydroxyl group of the nucleotide is substituted by methoxyl group.

The above content describes in detail the preferred embodiments of the present disclosure, but the present disclosure is not limited thereto. A variety of simple modifications can be made in regard to the technical solutions of the present disclosure within the scope of the technical concept of the present disclosure, including a combination of individual technical features in any other suitable manner, such simple modifications and combinations thereof shall also be regarded as the content disclosed by the present disclosure, each of them falls into the protection scope of the present disclosure.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A conjugate T having a structure represented by formula (601), (602), (603), (604), (605), (606) or (607):

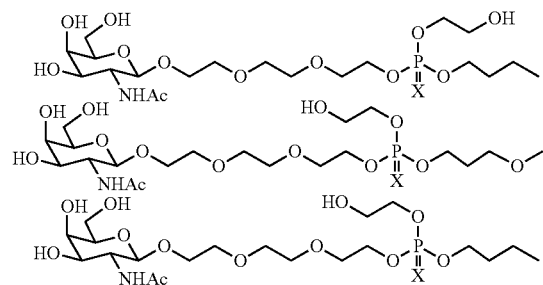

(601)

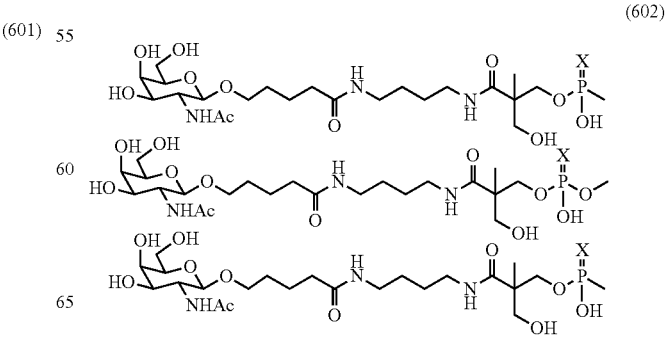

(602)

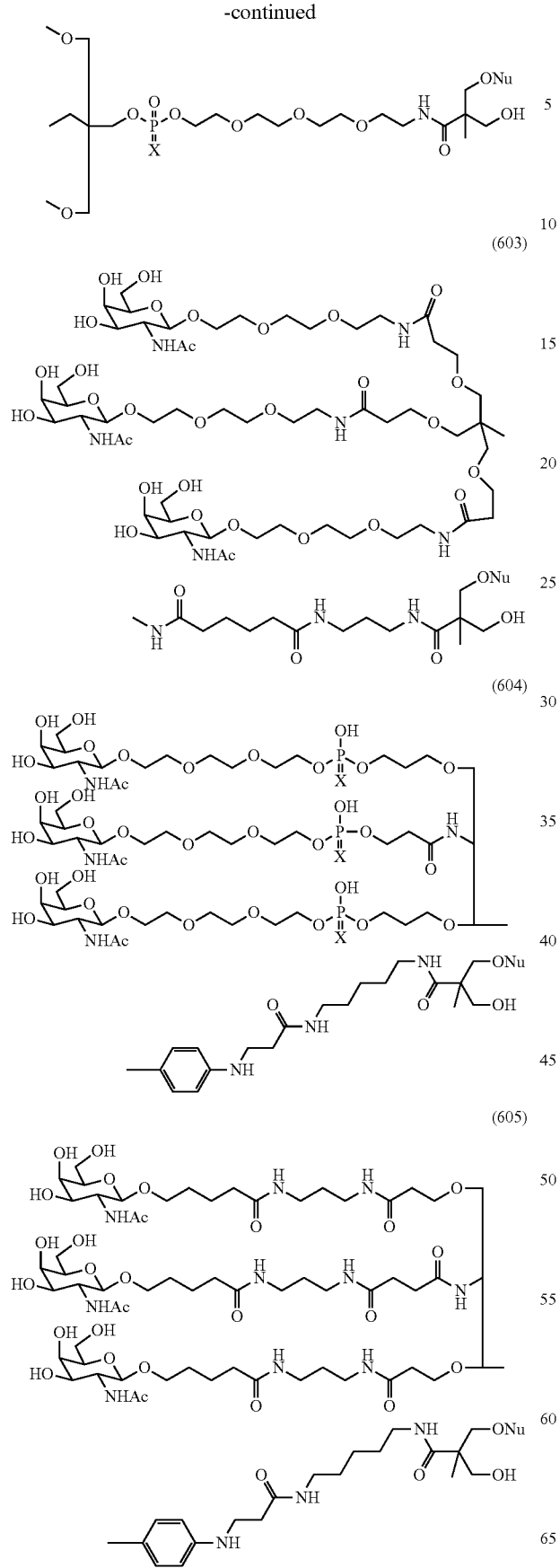
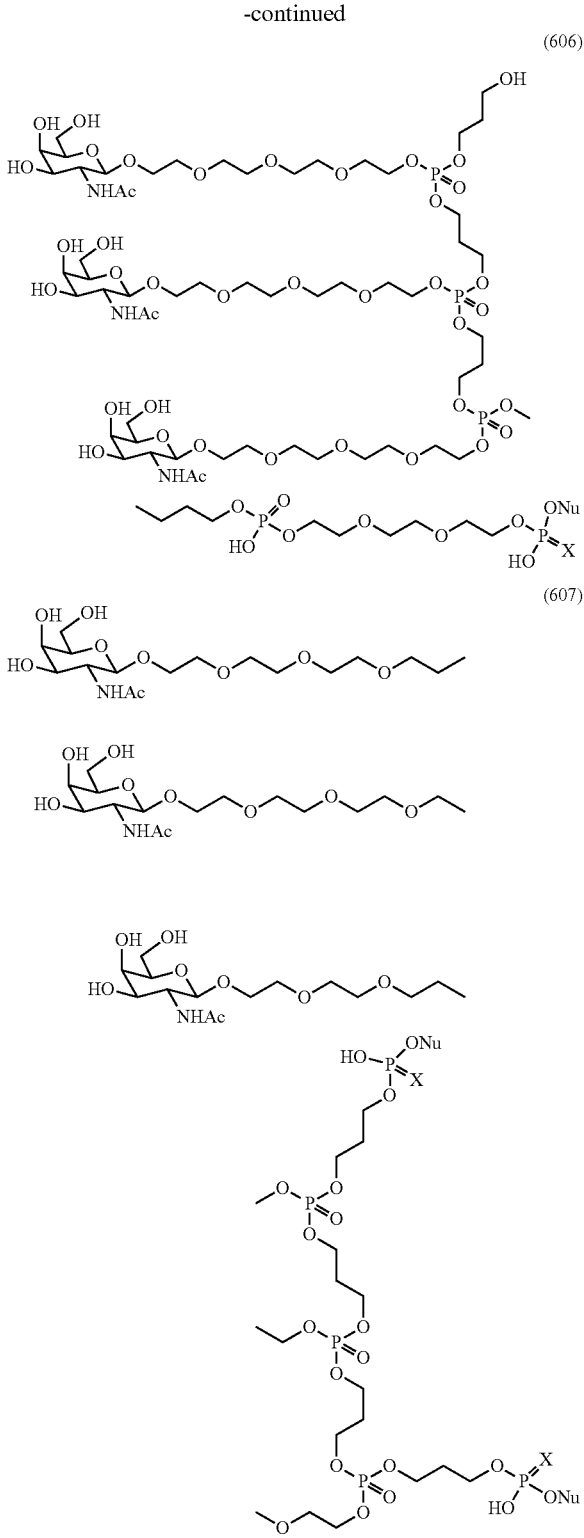
wherein
X on formula (601), (602), (603), (604), (605), (606) or (607) is O or S; and
Nu is an active drug small nucleic acid.
2. The conjugate T according to claim 1, wherein the nucleic acid is directed to a specific target gene.

3. The conjugate T according to claim 2, wherein the specific target gene is at least one selected from the group consisting of PCSK9, HBV, TTR and AGT.

4. The conjugate T according to claim 1, wherein the nucleic acid is an siRNA.

5. A conjugate T having a structure represented by formula (603):

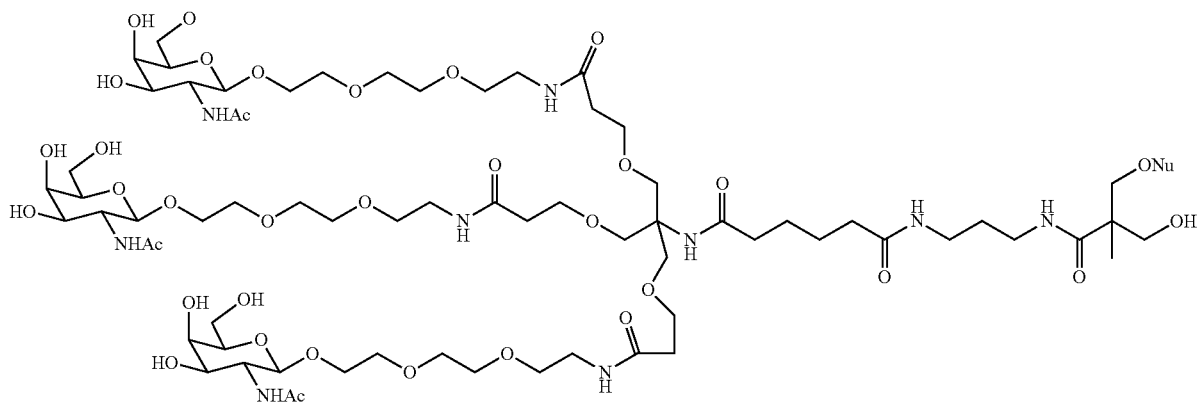

wherein
X on formula (601), (602), (603), (604), (605), (606) or (607) is O or S; and
Nu is an active drug small nucleic acid.

6. The conjugate T according to claim 5, wherein the nucleic acid is an siRNA.

* * * * *

UNITED STATES PATENT AND TRADEMARK OFFICE
CERTIFICATE OF CORRECTION

PATENT NO. : 12,150,997 B1  
APPLICATION NO. : 18/381402  
DATED : November 26, 2024  
INVENTOR(S) : Dong Yu Page 1 of 1

It is certified that error appears in the above-identified patent and that said Letters Patent is hereby corrected as shown below:

In the Specification

Please replace structure 602 starting at Column 68, Lines 55-66 and ending on Column 69, Lines 1-10 with

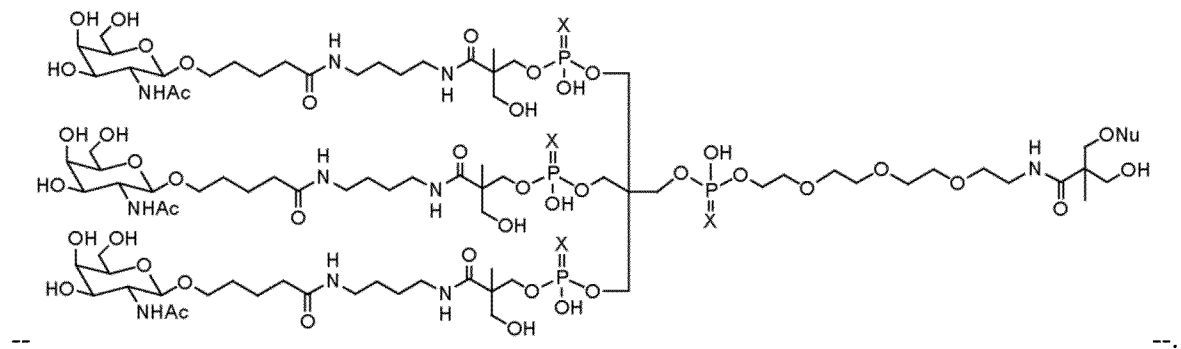
-- --.

In the Claims

Column 71, Claim 5, Lines 9-26: please replace formula (603) with

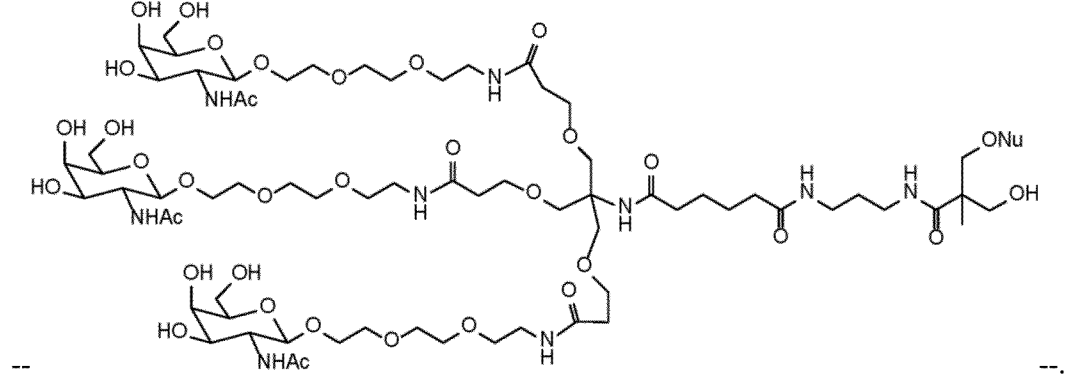
-- --.

Signed and Sealed this  
Fourth Day of February, 2025

Coke Morgan Stewart  
*Acting Director of the United States Patent and Trademark Office*